United States Patent
Nuijen et al.

(10) Patent No.: US 8,563,592 B2
(45) Date of Patent: *Oct. 22, 2013

(54) BLADDER CANCER TREATMENT AND METHODS

(75) Inventors: Bastiaan Nuijen, Amsterdam (NL); Ernie Pfadenhauer, Irvine, CA (US); Jos H. Beijnen, Amsterdam (NL); Dorla Mirejovsky, Irvine, CA (US); Guru Reddy, Irvine, CA (US); Luigi Lenaz, Newton, PA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/083,424

(22) Filed: Apr. 8, 2011

(65) Prior Publication Data

US 2011/0288143 A1 Nov. 24, 2011

Related U.S. Application Data

(60) Continuation-in-part of application No. 12/327,781, filed on Dec. 3, 2008, now abandoned, which is a continuation of application No. 11/096,566, filed on Apr. 1, 2005, now abandoned, which is a division of application No. 10/285,783, filed on Nov. 1, 2002, now Pat. No. 6,894,071, application No. 13/083,424, which is a continuation-in-part of application No. 12/396,158, filed on Mar. 2, 2009, now abandoned, which is a continuation of application No. 11/673,537, filed on Feb. 9, 2007, now abandoned.

(60) Provisional application No. 60/344,446, filed on Nov. 1, 2001, provisional application No. 60/771,678, filed on Feb. 9, 2006.

(51) Int. Cl.
 *A61K 31/404* (2006.01)
 *A61K 31/405* (2006.01)

(52) U.S. Cl.
 USPC .......................................... 514/414; 514/772

(58) Field of Classification Search
 USPC ........................................................ 514/414
 See application file for complete search history.

(56) References Cited

U.S. PATENT DOCUMENTS

| | | | |
|---|---|---|---|
| 4,871,542 A | 10/1989 | Vilhardt | |
| 4,898,729 A | 2/1990 | Miller et al. | |
| 5,079,257 A | 1/1992 | Speckamp et al. | |
| 5,216,011 A | 6/1993 | Paborji et al. | |
| 5,292,516 A | 3/1994 | Viegas et al. | |
| 5,346,703 A | 9/1994 | Viegas et al. | |
| 5,405,622 A | 4/1995 | Vernice et al. | |
| 5,550,110 A | 8/1996 | Cody et al. | |
| 5,612,359 A | 3/1997 | Murugesan | |
| 5,744,166 A | 4/1998 | Illum | |
| 5,749,845 A | 5/1998 | Hildebrand et al. | |
| 5,811,416 A | 9/1998 | Chwalisz et al. | |
| 5,814,330 A | 9/1998 | Putteman et al. | |
| 5,843,156 A | 12/1998 | Slepian et al. | |
| 5,942,209 A | 8/1999 | Leavitt et al. | |
| 5,993,846 A | 11/1999 | Friedman et al. | |
| 6,005,020 A | 12/1999 | Loomis | |
| 6,039,967 A | 3/2000 | Ottoboni et al. | |
| 6,087,396 A | 7/2000 | Roberts | |
| 6,123,965 A | 9/2000 | Jacob et al. | |
| 6,156,348 A | 12/2000 | Santos et al. | |
| 6,156,744 A | 12/2000 | Ross et al. | |
| 6,171,610 B1 | 1/2001 | Vacanti et al. | |
| 6,207,180 B1 | 3/2001 | Ottoboni et al. | |
| 6,894,071 B2 | 5/2005 | Nuijen et al. | |
| 2002/0082285 A1 | 6/2002 | Lebwohl | |
| 2003/0133954 A1 | 7/2003 | Nuijen et al. | |
| 2004/0009918 A1 | 1/2004 | Nedergaard et al. | |
| 2004/0138121 A1 | 7/2004 | Gulati | |
| 2005/0215615 A1 | 9/2005 | Nuijen et al. | |
| 2006/0257362 A1 | 11/2006 | Gulati | |
| 2007/0010570 A1 | 1/2007 | Nuijen et al. | |
| 2007/0059306 A1 | 3/2007 | Grosmaire et al. | |
| 2007/0185188 A1 | 8/2007 | Mirejovsky et al. | |
| 2009/0163570 A1 | 6/2009 | Mirejovsky et al. | |

FOREIGN PATENT DOCUMENTS

| | | |
|---|---|---|
| EP | 0 331 635 | 9/1989 |
| EP | 0 393 575 | 10/1990 |
| EP | 0 426 463 | 5/1991 |
| EP | 0 501 523 | 9/1992 |
| EP | 0 642 797 | 3/1995 |
| EP | 0 655 463 | 5/1995 |
| EP | 0 815 870 | 6/1997 |
| EP | 0 950 418 | 10/1999 |

(Continued)

OTHER PUBLICATIONS

Rajeshkumar et al. "Endothelini B receptor agonist, IRL 1620, enhances the anti-tumor efficacy of paclitaxel in breast tumor rats." Breast Cancer Research and Treatment, 2005, 94: 237-247.

(Continued)

*Primary Examiner* — John Pak

(74) *Attorney, Agent, or Firm* — K&L Gates LLP; Louis C. Cullman; Brent A. Johnson

(57) ABSTRACT

Therapeutic compositions comprising an indoloquinone compound and various bladder cancer treatments and methods are disclosed. More specifically, the compositions comprise an indoloquinone compound and a formulation vehicle. The formulation vehicle improves the solubility and stability of the indoloquinone compound. Additionally, the coating compositions can include coating agents that provide better adhesion of the coating composition to the bladder wall during intravesical delivery of the coating composition.

12 Claims, 6 Drawing Sheets

(56) References Cited

FOREIGN PATENT DOCUMENTS

| JP | 354151134 | 11/1979 |
|---|---|---|
| JP | 360163821 | 8/1985 |
| JP | 361189215 | 8/1986 |
| JP | 407215843 | 8/1995 |
| JP | 2000-256182 | 9/2000 |
| JP | 2001-010951 | 1/2001 |
| WO | 87/06227 | 10/1987 |
| WO | 96/19233 A2 | 6/1996 |
| WO | 97/26884 | 7/1997 |
| WO | 99/12548 | 3/1999 |
| WO | 99/12548 A1 | 3/1999 |
| WO | 99/65463 | 12/1999 |
| WO | 00/33816 | 6/2000 |
| WO | 00/67023 A1 | 11/2000 |
| WO | 00/67024 A1 | 11/2000 |
| WO | 01/00198 A2 | 4/2001 |
| WO | 01/91736 A2 | 12/2001 |
| WO | 03/009805 A2 | 2/2003 |
| WO | 03/037314 A1 | 5/2003 |
| WO | 03/045434 A2 | 6/2003 |
| WO | 03/092731 A1 | 11/2003 |
| WO | 2007/092963 | 8/2007 |
| WO | 2007/092964 | 8/2007 |

OTHER PUBLICATIONS

Robertson et al. "Factors affecting sensitivity to E09 in rodent and human tumour cells in vitro: DT-diaphorase activity and hypoxia", European Journal of Cancer, 1994, pp. 1013-1019, vol. 30A, No. 7.
Ross et al. "Enzymology of bioreductive drug activation." Br J Cancer 1996;Suppl 27:S1-8.
Saeki et al. "[Ala1,3,11,15]Endothelin-1 Analogs with ETB Agonistic Activity." Biochemical and Biophysical Research Communications, vol. 179, No. 1, 1991, pp. 286-292.
Santos et al. "Expression of cell-cycle regulatory proteins and their prognostic value in superficial low-grade urothelial cell carcinoma of the bladder." Eur J Surg Oncol 2003;29:74-80.
Santos et al. "Ki-67 index enhances the prognostic accuracy of the urothelial superficial bladder carcinoma risk group classification." Int J Cancer 2003;105: 267-72.
Sartorelli et al. "Mitomycin C: a prototype bioreductive agent." Oncol Res 1994;6:501-8.
Saunders et al., "The relative importance of NADPH:cytochrome c (P450) reductase for determining the sensitivity of human tumor cells to the indoloquinone E09 and related analogues lacking functionality at the C-2 and C-3 positions." Biochem. Pharmacol., 2000, 59:993-996.
Schellens et al., "Phase I and pharmacologic study of the novel indoloquinone bioreductive alkylating cytotoxic drug E09", Journal of the National Cancer Institute, 1994, pp. 906-912, vol. 86, No. 12.
Schlager et al., "MMC is not metabolized by but is an inhibitor of human kidney NAD(P)H:quinone acceptor) oxidoreductase." Cancer Chemother. Pharmacol., 1988, 22:126-130.
Siegel et al., "Immunohistochemical detection of NAD(P)H:Quinone oxidoreductase in human lung and lung tumors." Clin. Cancer Res., 1998, 4:2065-2070.
Siegel et al., "Metabolism of MMC by NQ01: role in MMC induced DNA damage and cytotoxicity in human colon carcinoma cells." Cancer Res., 1990, 50:7483-7489.
Siegel et al., "PH dependent inactivation of NQ01 by MMC and porfiromycin." Mol. Pharmacol., 1993, 44:1128-1134.
Smitskamp-Wilms et al., "Chemosensitivity to the indoloquinone E09 is correlated with DT-diaphorase activity and its gene expression." Biochem. Pharmacol., 1994, 47(8):1325-1332.
Smitskamp-Wilms et al., "NQ01 activity in normal and neoplastic human tissues: An indicator of sensitivity to bioreductive agents?" Br. J. Cancer, 1995, 72:917-921.
Sonveaux et al. "Endothelini-1 is a critical mediator of myogenic tone in tumor arterioles: implications for cancer treatment" Cancer Research 64, 3209-3214, 2004.

Tolley et al. "The effect of intravesical mitomycin C on recurrence of newly diagnosed superficial bladder cancer: a further report with 7 years of follow up." J Urol 1996;155:1233-8.
Traver et al., "NAD(P)H:quinine oxidoreductase gene expression in human colon carcinoma cells: Characterisation of a mutation which modulates NQ01 activity and mitomycin sensitivity." Cancer Res., 1992, 52:797-802.
Vainchtein et al. "Quantitative analysis of EO9 (apaziquone): and its metabolite EO5a in human plasma by high-performace liquid chromatography under basic conditions coupled to electrospray tandem mass spectrometry", Journal of Mass Spectrometry. 2006, pp. 1268-1276, vol. 41.
Vainchtein et al., "Stability experiments in human urine with EO9 (apaziquone): A novel anticancer agent for the intravesical treatment of bladder cancer", Journal of Pharmaceutical and Biomedical Analysis, 2006, pp. 285-292, vol. 43.
Van Der Heijden et al. "Phase II Marker Lesion Study with Intravesical Instillation of Apaziquone for Superficial Bladder Cancer: Toxicity and Marker Response." The Journal of Urology, vol. 176, 1349-1353, Oct. 2006.
Van Der Schoot et al. "EO-9 bladder instillations: Formulation selection based on stability characteristics and in vivo stimulation studies." International Journal of Pharmaceutics 329, 2007, 135-141.
Van Der Schoot et al., "Development of a bladder instillation of the indoloquinone anticancer agent EO9 using tert-butyl alcohol as lyophilizatio vehicle", Chapter 1.1, Pharmaceutical development of investigational anticancer agents: focus on EO9, AP5346, and GMP implications, 2006, pp. 19-44.
Walton et al., "The role of NAD(P)H:quinine reductase (EC 16.99.2, NQO1) in the reductive bioactivation of the novel indoloquinone antitumour agent E09." Cancer Commun., 1991, 3(7):199-206.
Wardman et al. "Radicals from one-electron reduction of nitro compounds, aromatic N-oxides and quinones: the kinetic basis for hypoxia-selective, bioreductive drugs." Biochem Soc Symp 1995;61:171-94.
Workman et al. "The experimental development of bioreductive drugs and their role in cancer therapy." Cancer Met Rev 1993;12:73-82.
Workman "Enzyme directed bioreductive drug development revisited: a commentary on recent progress and future prospects with emphasis on quinine anticancer drugs and quinine metabolizing enzymes, particularly NQO1." Oncol. Res., 1994, (10/11) 6:461-475.
Wu "Recent discovery and development of endothelin receptor antagonists." Expert Opinion on Therapeutic Patents, 2000, Ashley Publications Ltd.
Wulfing et al. "Endothelin-1, Endothelin-A- and Endothelin-B-receptor expression in preinvasive and invasive breast disease." Oncology Reports 11, 791-796, 2004.
Yamashita et al. "A Large Amount of Endothelin-1 is Present in Human Breast Cancer Tissues." Research Communications in Chemical Pathology and Pharmacology, vol. 74, No. 3, Dec. 1991.
Yamashita et al. "Abundant Expression of Immunoreactive Endothelin 1 in Mammary Phyllodes Tumor: Possible Paracrine Role of Endothelin 1 in the Growth of Stromal Cells in Phyllodes Tumor." Cancer Research 52, 4046-4049, 1992.
Yanagisawa et al. "A novel potent vasoconstrictor peptide produced by vascular endothelial cells." Nature vol. 332, 1988.
Yen et al., "Different pH dependency of mitomycin C activity in monolayer and three dimensional cultures." Pharmaceut. Res., 1996, 13(12):1887-1891.
Sylvester et al. "A single immediate postoperative instillation of chemotherapy decreases the risk of recurrence in patients with stage Ta T1 bladder cancer: a metaanalysis of published results of randomized clinical trials." J. Urol. 2004, 171 (6 Pt 1):2186-90.
Chemical Abstracts 120:62141, (1994).
Cummings et al. "Pharmacological and Biochemical Determinants of the Antitumour Activity of the Indoloquinone EO9." Biochemical Pharmacology, vol. 55, pp. 253-260, 1998.
De Vries et al. "A systematic study on the chemical stability of the novel indoloquinone antitumour agent EO9." International Journal of Pharmaceutics, 100 (1993) 181-188.
Medline abstract 2001071878, (2001).

(56) References Cited

OTHER PUBLICATIONS

Office Action issued Jun. 23, 2011 in U.S. Appl. No. 12/327,781, (2011).
Airley et al. "GLUT-1 and CAIX as intrinsic markers of hypoxia in carcinoma of the cervix: relationship to pimonidazole binding." Int J Cancer 2003;104:85-91.
Alanen et al. "Augmented expression of endothelin-1, endothelini-3 and the endothelin-B receptor in breast carcinoma." Histopahtology 2000, 36, 161-167.
Arellano et al. "Influence of propylene glycol and isopropyl myristate on the in vitro percutaneous penetration of diclofenac sodium from carbopol gels." European Journal of Pharmaceutical Sciences, 7 (1998) 129-135.
Bagnato et al "Endothelin Receptor Blockade Inhibits Proliferation of Kaposi's Sarcoma Cells." American Journal of Pathology, vol. 158, No. 3, Mar. 2001.
Bagnato et al. "Expression of Endothelin 1 and Endothelin A Receptor in Ovarian Carcinoma: Evidence for an Autocrine Role in Tumor Growth." Cancer Research 59, 720-727, Feb. 1, 1999).
Basu et al. "Immunohistochemical analysis of NAD(P)H:quinone oxidoreductase and NADPH cytochrome P450 reductase in human superficial bladder tumors: relationship between tumor enzymology and clinical outcome following intravesical mitomycin C therapy." Int J Cancer 2004;109:703-9.
Battistini et al. "Endothelins: A Quantum Leap Forward." DN&P 8(6), Aug. 1995.
Belcourt et al. "Differential toxicity of mitomycin C and porfiromycin to aerobic and hypoxic Chinese hamster ovary cells overexpressing human NADPH:cytochrome c (P-450) reductase." Proc Natl Acad Sci USA 1996;93:456-60.
Bell et al. "A Comparative Study of Tumour Blood Flow Modification in Two Rat Tumour Systems Using Endotelin-1 and Angiotensin II: Influence of Tumour Size on Angiotensin II Response." Int. J. Cancer: 67, 730-738, 1996.
Bell et al. "Effect of Endothelin-1 and Sarafotoxin S6c on Blood Flow in a Rat Tumor." Journal of Cardiovascular Pharmacology, 26(Suppl. 3) S222-S225, 1995.
Bell et al. "Modification of Blood Flow in the HSN Tumour and Normal Tissues of the Rat by the Endothelin ETB Receptor Agonist, IRL 1620." Int. J. Cancer: 80, 295-302, 1999.
Bell et al. "Tumour blood flow modification by endothelin-related peptides in the rat HSN fibrosarcoma." British Journal of Cancer (1996) 74, S161-S163.
Bell et al. "Vascular Response of Tumour and Normal Tissues to Endothelin-1 Following Antagonism of ETA and ETB Receptors in Anaesthetised Rats." Int. J. Cancer: 73, 283-289, 1997.
Bhalla et al. "Potentiation of morphine analgesia by BQ123, an endothelin antagonist." Peptides 23, 2002, 1837-1845.
Bhargava et al. "Modification of Brain and Spinal Cord Dopamine D1 Receptors Labeled with [3H]SCH 23390 After Morphine Withdrawl from Tolerant and Physically Dependent Rats1." The Journal of Pharmacology and Experimental Therapeutics, vol. 252, No. 3, 1990.
Bladder Cancer article, Cancer Research UK.
Blanchet et al. "Prospective evaluation of Ki-67 labeling in predicting the recurrence and progression of superficial bladder transitional cell carcinoma." Eur Urology 2001;40:169-75.
Bradford "A rapid and sensitive method for the quantification of microgram quantities of protein utilizing the principle of protein-dye binding." Anal. Biochem., 1976, 72:248-254.
Brooks et al. "SB 234551, a Novel Endothelin-A Receptor Antagonist, Unmasks Endothelin-Induced Renal Vasodilation in the Dog." Journal of Cardiovascular Pharmacology, 31(Suppl. 1) S339-S341, 1998.
Bubendorf et al. "Tissue microarray (TMA) technology: miniaturized pathology archives for high-throughput in situ studies." Journal of Pathology 2001;195: 72-9.
Butler, J., et al., "The autooxidation of reduced forms of E09." Free. Rad. Res., 1996, 25(2):141-148.

Carmeliet et al. "Angiogenesis in cancer and other diseases." Nature, vol. 407, Sep. 14, 2000.
Cemazar et al. "The endothelin B (ETB) receptor agonist IRL 1620 is highly vasoconstrictive in tow syngeneic rat tumour lines: potential for selective tumour blood flow modification." British Journal of Cancer, 2005, 93, 98-106.
Chang et al. "Expression of the human erythrocyte glucose transporter in transitional cell carcinoma of the bladder." Urology 2000;55:448-52.
Chaplin et al. "Modification of Tumour Blood Flow: Current Status and Future Directions." Seminars in Radiation Oncology, vol. 8, No. 3, 1998, pp. 151-163.
Chemical Abstracts 120: 62141, 1994.
Chemical abstracts 122:17023 (1995).
Choudry et al., "A Novel Strategy for NQ01 (NAD(P)H:quinone oxidoreductase, EC 1.6.99.2) Mediated Therapy of Bladder Cancer Based on the Pharmacological Roperties of E09", British Journal of Cancer, 2001, pp. 1137-1146, vol. 85, No. 8.
Connors "Bioreductive agents, hypoxic cells and therapy." Eur. J. Cancer, 1996, 32A(11):1833-1834.
Cummings et al., "Pharmacological and biochemical determinants of the antitumor activity of the indoloquinone E09", Biochemical Pharmacology, 1998, pp. 253-260, vol. 55, No. 3.
Cummings et al., "Enzymology of MMC metabolic activation in tumor tissue. Implications for enzyme directed bioreductive drug development." Biochem. Pharmacol., 1998, 56:405-414.
Danson et al. "DT-diaphorase: a target for new anticancer drugs." Cancer Treat Rev 2004;30:437-49.
Davar et al. "Behavioral signs of acute pain produced by application of endothelin-1 to rat sciatic nerve." NeuroReport 9, 2279-2283, 1998.
Davenport et al. "Classification of endothelin receptors and antagonists in clinical development." Clinical Sciences, 2002, 103 (Suppl. 48) 15-35.
De Ascentiis et al., "Mucoadhesion of poly(2-hydroxyethyl methacrylate) is improved when linear poly(ethylene oxide) chains are added to the polymer network." 1995, Journal of Controlled Release, vol. 33, pp. 197-201.
De Vries et al., A systematic study on the chemical stability of the novel indoloquinone antitumor agent EO9; abstract, International Journal of Pharmaceutics, 1993.
De Vries et al., Pharmaceutical development of a parenteral lyophilized formulation of the novel indoloquinone antitumor agent EO9; abstract, Cancer Chemotherapy and Pharmacology, 1994, vol. 34.
Dehn et al. "Development of a new isogenic cell-xenograft system for evaluation of NAD(P)H:quinone oxidoreductase-directed antitumor quinones: evaluation of the activity of RH1." Clinical Cancer Res 2004;10:3147-55, (2004).
Del Bufalo et al. "Endothelin-1 acts as a survival factor in ovarian carcinoma cells." Clinical Science, 2002, 103 (Suppl. 48), 3025-3055.
Dirix et al., "E09 phase II study in advanced breast, gastric, pancreatic and colorectal carcinoma by the early clinical studies group." Eur. J. Cancer, 1996, 32A(11):2019-2022.
Dong Li et al., "Distribution of DT-diaphorase and cytochrome P450 reductase in human bladder tissues and tumors", Proceedings of the American Association for Cancer Research Annual, 2001, p. 648, vol. 42.
Douglas et al. "Pharmacological evidence for the presence of three distinct funcational endothelini receptor subtypes in the rabbit lateral saphenous vein." British Journal of Pharmacology, 1995, 114, 1529-1540.
Duggan et al. "Protection against aspirin-induced human gastric mucosal injury by bosentan, a new endothelin-1 receptor antagonist." Aliment Pharamcol Ther 1991: 13: 631-635.
Fabricio et al. "Essential role for endothelini ETB receptors in fever induced by LPS (E. coli) in rats." British Journal of Pharmacology, 1998, 125, 542-548.
Fitzsimmons et al., "Reductase enzyme expression across the national Cancer Institute tumor cell line panel: Correlation with sensitivity to MMC and E09." J. Nat. Cancer Inst., 1996, 88(5):259-269.

(56) References Cited

OTHER PUBLICATIONS

Fukumura et al. "Role of Nitric Oxide in Tumor Microcirculation." American Journal of Pahtology, vol. 150, No. 2, 1997.

Gulati "Preface." Advanced Drug Delivery Reviews 40 (2000) 129-130.

Gulati et al. "Role of ET and NO in resuscitative effect of diaspirin cross-linked hemoglobin after hemorrhage in rat." The American Physiological Society, 1997.

Gutierrez "Mechanism of bioreductive alkylation. The example of diazaquinone (AZQ)." Free Radical Bio. Med., 1989, 6:405-445.

Hendriks et al., "E09: A novel bioreductive alkylating indoloquinone with preferential solid tumor activity and lack of bone marrow toxicity in preclinical models." Eur. J. Cancer, 1993, 29A(6):897-906.

Herr "Intravesical therapy—a critical review." Urol. Clin. N. Am., 1987, 14(2):399-404.

Hirst et al. "The radiosensitizer nicotinamide inhibits arterial vasocontriction." The British Journal of Radiology, 67, 795-799, 1994.

Hodnick et al., "Measurement of dicumarol sensitive NADPH: (menadione cytochrome c) oxidoreductase activity results in an artificial assay of DT-diaphorase in cell sonicates." Anal. Biochem., 1997, 252:165-168.

Hoskin et al. "GLUT1 and CAIX as intrinsic markers of hypoxia in bladder cancer: relationship with vascularity and proliferation as predictors of outcome of ARCON." British Journal of Cancer 2003;89:1290-1297.

Hussain et al. "Long-term results of a phase II study of synchronous chemoradiotherapy in advanced muscle invasive bladder cancer." British Journal of Cancer 2004;90:2106-2111.

Inoue et al. "The human endothelin family: Three structurally and pharmacologically distinct isopeptides predicted by three separate genes." Proc. Natl. Acad. Sci., vol. 86, pp. 2863-2867, 1989.

Jarvis et al. "ABT-627, an endothelin ETA receptor-selective antagonist, attenuates tactile aooldynia in a diabetic rat model of neuropathic pain." European Journal of Pharmacology 388, 2000, 29-35.

Jordan et al. "Changes in tumor oxygenation/perfusion induced by the no donor, isosorbide dinitrate, in comparison with carbogen: monitoring by EPR and MRI." Int. J. Radiation Oncology Biol. Phys., vol. 48, No. 2, pp. 565-570, 2000.

Jordan et al. "Insulin Increases the Sensitivity of Tumors to Irradiation: Involvement of an Increase in Tumor Oxygenation Mediated by a Nitric Oxide-dependent Decrease of the Tumor Cells Oxygen Consumption." Cancer Research 62, 2555-3561, 2002.

Jordan et al. "Potentiation of Radiation-Induced Regrowth Delay by Isosorbide Dinitrate in FSAII Murine Tumors." Int. J. Cancer: 103, 138-141, 2003.

Kantoff et al., "Bladder Cancer, Neoplasms of the Genitourinary Tract", Chapter 107, pp. 1543-1558.

Kennedy et al., "Proliferation and hypoxia in human squamous cell carcinoma of the cervix: First report of combined immunohistochemical assays." Int. J. Radiat. Oncol. Biol. Phys., 1997, 37(4):897-905.

Kikuchi et al. "Decreased ETB Receptor Expression in Human Metastatic Melanoma Cells." Biochemical and Biophysical Communications: 219, 734-739, 1996.

Kim et al. "The importance of DT-diaphorase and hypoxia in the cytotoxicity of RH1 in human breast and non-small cell lung cancer cell lines." Anticancer Drugs 2004;15:71-7.

Kroodsma et al. "Endothelins: possibly a new pharmacological starting point in cardiovascular disease, kidney disease and oncologicial conditions." Ned Tijdschr Geneeskd. Sep. 20, 1997;141(38):1806-10.

Kuin et al., "Potentiation of anti-cancer activity at low intratumoural pH induced by the mitochondrial inhibitor m-iodobenzylguanidine (MIBG) and its analogue benzylguanidine (BG)." Br. J. Cancer, 1999, 79(5/6)193-801.

Kurbel et al. "Endothelin-secreting tumors and the idea of the pseudoectopic hormone secretion in tumors." Madical Hypotheses, 1999, 54(4), 329-333.

Lahav et al. "An endothelin receptor B antagonist inhibits growth and induces cell death in human melanoma cells in vitro and in vivo." Proc. Natl. Acad. Sci. USA, vol. 96, pp. 11496-11500, 1999.

Laviada et al., "Phosphatidylcholine-phospholipase C mediates the induction of nerve growth factor in cultured glial cells." FEBS Letters, 1995, 364:301-304.

Lenaz et al. "IRL-1620 increases the efficacy of radiation treatment in mice bearing lymphoma cell induced tumors." Symposium of the International-Society-of-Molecular-Evolution; Guanacaste, Costa Rica, Jan. 8-12, 2001.

Levin et al. "Immunologic Analysis of a Spinal Cord-Biopsy Specimen from a Patient with Human T-Cell Lymphotropic Virus Type I-Associated Neurologic Disease." New England Journal of Medicine 336(12):839-845, 1997.

Li et al. "Distribution of DT-diaphorase and reduced nicotinamide adenine dinucleotide phosphate: cytochrome p450 oxidoreductase in bladder tissues and tumors." J Urol 2001;166:2500-5.

Li et al., "Distribution of DT-diaphorase and cytochrome P450 reductase in human bladder tissues and tumors." Proceedings of the American Association for Cancer Research Annual Meeting, Mar. 2001, 42:648.

Maffezzini et al., "Up-front chemotherapy for low stage low grade recurrent bladder cancer." L. Urol., 1996, 155:91-93.

Maliepaard et al., "Indoloquinone E09: DNA interstrand cross linking upon reduction by DT-diaphorase or xanthine oxidase." Br. J. Cancer, 1995, 71:836-839.

Malkinson et al., "Elevated NQO1 activity and messenger RNA content in human non small cell lung carcinoma—Relationship to the response of lung tumor xenografts to MMC." Cancer Res., 1992, 52(12):4752-4757.

Martinive et al. "Reversal of temporal and spatial heterogeneities in tumor perfusion identifies the tumor vascula tone as a tunable variable to improve drug delivery." Mol Cancer Ther,2006;5(6).

Matsumaru et al. "Bosentan, a novel synthetic mixed-type endothelin receptor antagonist, attenuates acute gastric mucosal lesions induced by indomethacin and HCl in the rat: Role of endogenous endothelin-1." J Gastroenterol 1997; 32:164-170.

Medline Abstract 2001071878 (Entered Medline Jan. 4, 2001).
Medline Abstract 92362735, 1992.

Mossoba et al., "Mechanism for the reductive activation of diazaquinone." J. Pharm. Sci., 1985, 74(12):1249-1254.

Newling "Intravesical therapy in the management of superficial transitional cell carcinoma of the bladder: the experience of the EORTC GU group." Br. J. Cancer, 1990, 61:497-499.

Nicolaus "Symbiotic Approach to Drug Design, Decision Making in Drug Research", 1983, pp. 173-186.

Nieder et al. "The role of pentoxifylline as a modifier of radiation therapy." Cancer Treatment Reviews 2005, 31, 448-455.

Nucci et al. "Pressor effects of circulating endothelin are limited by its removal in the pulmonary circulation and by the release of prostacyclin and endothelium-derived relaxing factor." Proc. Natl. Acad. Sci. USA, vol. 85, pp. 9797-9800, Dec. 1988.

Okada et al. "BQ-788, A Selective Endothelin ETB Receptor Antagonist." Cardiovascular Drug Reviews, vol. 20, No. 1, pp. 53-66, 2002.

Oosterhuis et al. "MIB-1 as a proliferative marker in transitional cell carcinoma of the bladder: clinical significance and comparison with other prognostic factors." Cancer 2000;88:2598-605.

Oosterlink, et al., "A prospective European Organization for Research and Treatment of Cancer Genitourinary Group randomized trial comparing transurethral resection followed by a single instillation of epirubicin or water in single stage Ta, T1 papillary carcinoma of the bladder." J. Urol., 1993, 149:749-752.

Pan et al., "Enzymatic and pH modulation of MMC induced DNA damage in MMC resistant HCT 116 human colon cancer cells." Mol. Pharmacol., 1993, 43:870-877.

Parfitt "Analgesics Anti-inflammatory Drugs and Antipyretics." Martindale, The Complete Drug Reference 32 Edition (Edited by: Parfitt K). London, Pharmaceutical Press 1999 , 61-62.

Patel et al. "Stimulation or endothelin-1 secretion by human breast cancer cells through protein kinase A activation: a possible novel paracrine loop involving breast fibroblast-derived prostglandin E21." Molecular and Cellular Endocrinology 126, 1997, 143-151.

(56) References Cited

OTHER PUBLICATIONS

Phillips "Bioreductive activation of a series of analogues of 5-aziridinyl-3hydroxymethyl-1-methyl-2-[1H-indolo-4,7-dione] prop-(3-en-a-ol (E09) by human NQO1." Biochem. Pharmacol., 1996, 52:711-171.
Phillips "Inhibition of DT-diaphorase (NAD(P)H:quinine oxidoreductase, EC 1.6.99.2) by 5,6-dimethylxanthenone-4-acetic acid (DNIXAA) and flavone-8acetic acid (FAA): Implications for bioreductive drug development." Biochem. Pharmacol., 1999, 58:303-310.
Phillips et al. "Evaluation of a novel in vitro assay for assessing drug penetration into avascular regions of tumors." Br. J. Cancer, 1998, 77(12):2112-2119.
Phillips et al., "In vitro activity of the novel indoloquinone Eo-9 and the influence of pH on cytotoxicity." Br. J. Cancer, 1992, 65:359-364.
Plumb et al. "DT-diaphorase protects cells from the hypoxic cytotoxicity of indoloquinone EO9." Br J Cancer 1994;70:1136-43.
Plumb et al. "Unusually marked hypoxic sensitization to indoloquinone EO9 and mitomycin C in a human colon-tumor cell line that lacks DT-diaphorase activity." Int J Cancer 1994;56:134-9.
Puri et al. "Phase I clinical evaluation of intravesical EOquin (EO9) against superficial bladder cancer: Preliminary results." Clinical Cancer Res 2003;9:6248S-9S.
Puri et al. "Phase I/II Pilot Study of Intravesical Apaziquone (EO9) for Superficial Bladder Cancer." The Journal of Urology, vol. 176, 1344-1348, Oct. 2006.
Rai et al. "Evidence for the involement of ETB receptors in ET-1-induced changes in blood flow to the rat breast tumor." Cancer Chemother Pharmacol, 2003, 51:21-28.
Choudry et al. "A novel strategy for NQO1 (NAD(P)H:quinone oxidoreductase, EC 1.6.99.2) mediated therapy of bladder cancer based on the pharmacological properties of EO9." British Journal of Cancer, 2001, 85(8), 1137-1146.
Li et al. "Distribution of DT-diaphorase and reduced nicotinamide adenine dinucleotide phosphate: cytochrome P450 oxidoreductase in bladder tissues and tumors." The Journal of Urology, vol. 166, 2500-2505, 2001.
Palit et al. "Immunodetection of GLUT-1 and NQO1 (NAD(P)H: Quinone oxidoreductase) in superficial bladder cancer." British Journal of Cancer, 2003, vol. 88, Suuplement 1, p. S30, item P24.
Office Action issued in AU Application No. 2007213476.
Chaplin, David J., Ph.D. Session E: Bioreductive Therapies: Keynote Address: Bioreductive Therapy. Int. J. Radiation Oncology Biol. Phys., vol. 22, pp. 685-687 (1992).

0.5mg/ml EDTA   4 ml  } A
NaHCO₃          200mg }    } B
1,2-Propyldiol (PG)  2,4 or 6 ml }
H₂O respectively     4,2 or 0 ml }    } D   Mix at 37°C for 2-6 h EO9             2 mg  }
Mannitol        12.5 mg } C
NaHCO3          5 mg  }

Mixture D + WFI 1:1  ⟹  Ready for use

Non drug treated controls:
Thickness of MCL = 56.01 ± 3.63 μm

MCL one hour after treatment with
EO9 in 0.1% DMSO: Thickness of
MCL = 58.80 ± 2.50 μm MCL one hour after treatment with
EO9 in 30% PG: Thickness of
MCL = 29.01 ± 1.78 μm

BLADDER CANCER TREATMENT AND METHODS

CROSS-REFERENCE TO RELATED APPLICATIONS

This application is a continuation-in-part and claims priority pursuant to 35 U.S.C. 120 to U.S. patent application Ser. No. 12/327,781, filed Dec. 3, 2008, a continuation that claims priority to U.S. patent application Ser. No. 11/096,566, filed Apr. 1, 2005, a divisional that claims priority to U.S. patent application Ser. No. 10/285,783, filed Nov. 1, 2002, now U.S. Pat. No. 6,894,071, a U.S. Non-Provisional that claims priority to U.S. Provisional Application 60/344,446, filed Nov. 1, 2001, and to U.S. patent application Ser. No. 12/396,158, filed Mar. 2, 2009, a continuation that claims priority to U.S. patent application Ser. No. 11/673,537, filed Feb. 9, 2007, a U.S. Non-Provisional that claims priority to U.S. Provisional Application 60/771,678 filed Feb. 9, 2006, each of which is incorporated by reference in its entirety.

FIELD OF THE INVENTION

The present invention relates to the treatment of bladder cancer using Apaziquone formulations and methods. The present invention can take advantage of propylene glycol concentrations and/or NAD(P)H:quinone oxidoreductase-1 (NQO1), Cytochrome P450 Oxidoreductase (P450R) and Glucose transporter 1 (Glut-1) protein expression in human transitional cell carcinoma of the bladder to offer individually targeted bladder cancer treatments.

BACKGROUND OF THE INVENTION

Bladder cancer is the seventh most common cancer worldwide. In 2006, there were an estimated 280,000 cases of bladder cancer in Europe and more than 60,000 new cases were expected in the United States.

The most common type of bladder cancer (about 90%) is transitional cell carcinoma (TCC) which derives from the urothelium, the cellular lining of the urethral system (ureters, bladder and urethra). Transitional cell carcinoma (TCC) can be classified as either superficial (pTa and pT1), meaning that tumor involvement is limited to the mucosal or submucosal layer of the urothelium, or muscle invasive ($\geq$pT2). About 75% of newly detected bladder cancers are superficial at initial presentation, i.e., without muscle invasion. More specifically, superficial transitional cell carcinomas consist of papillary tumors that are confined to the mucosa (Ta), papillary or sessile tumors extending into the lamina propria (T1) and carcinoma in situ (CIS).

Superficial bladder cancers can be stratified into prognostic risk classes according to tumor stage, grade, size, number, and recurrence pattern. Low-stage, low-grade primary tumors (stage Ta, grades G1-G2) have a 30% recurrence rate over 2 years and do not usually progress to muscle invasion, while at the other extreme, multiple, highly recurrent or large T1 G3 tumors have up to a 70%-80% recurrence rate and a 10%-30% progression rate to a muscle-invasive stage. Carcinoma in situ (CIS) presents the highest risk of tumor progression.

Management of superficial bladder cancer may be achieved by transurethral resection, an endoscopic surgical removal of all visible lesions. Transurethral resection of bladder tumor (TUR-BT) is often followed by a course of adjuvant intravesical chemotherapy or immunotherapy with the aim of both eradicating remaining tumor cells and preventing tumor recurrence. See, e.g., Herr, H. W., Intravesical therapy—a critical review, Urol. Clin. N. Am. 14: 399-404 (1987). The validity of such a treatment is supported by the significant reduction in superficial tumor recurrence observed following adjuvant chemotherapy, when compared to TUR-BT alone. Although anti-neoplastics (Mitomycin C [MMC], epirubicin and thioTEPA) and immunotherapy (BCG) administered intravesically are effective at reducing tumor recurrence rates, it is unclear whether disease progression to muscle invasive tumors is prevented. See, e.g., Newling, D., Intravesical therapy in the management of superficial transitional cell carcinoma of the bladder: the experience of the EORTC GU group, Br. J. Cancer 61: 497-499 (1990); Oosterlink, et al., A prospective European Organization for Research and Treatment of Cancer Genitourinary Group randomized trial comparing transurethral resection followed by a single instillation of epirubicin or water in single stage Ta, T1 papillary carcinoma of the bladder, J. Urol. 149: 749-752 (1993). This observation in conjunction with the fact that mortality from bladder cancer is still high underscores the need to develop more effective therapeutic agents (Oosterlink et al. 1993). As such, there is a need to develop either more potent and/or less toxic agents against TCC or to use current therapeutics better in terms of targeting treatment to individuals (or pathological subgroups) that are likely to benefit.

Mitomycin C (MMC) is a naturally occurring quinone based anti-neoplastic agent that belongs to a class of compounds known as bioreductive drugs. Although designed in principle to eradicate hypoxic cells that reside in poorly perfuse regions of solid tumors, bioreductive drugs, can also target aerobic portions of tumors. The ability of quinone based bioreductive drugs to eradicate aerobic or hypoxic cells is largely determined by a complex relationship between tumor enzymology including the presence of reductases and hypoxia. In general, bioreductive drugs are pro-drugs that require metabolic activation to generate cytotoxic metabolites. Several reductases have been implicated in the activation of bioreductive drugs although considerable attention has been paid to the enzymes Cytochrome P450 reductase (P450R) and NAD(P)H:Quinone oxidoreductase-1 (NQO1). With regards to measurement of hypoxia, endogenous markers such as Glucose transporter 1 (Glut-1) or carbonic anhydrase IX (CAIX) have been shown to correlate with exogenous hypoxia markers such as pimonidazole. Thus, the relationship between tumor hypoxia and the expression of two key reductases in superficial and invasive transitional cell carcinomas (TCC) of the bladder is of key importance.

MMC is activated to a cytotoxic species by cellular reductases although the role of specific reductase enzymes involved in bioreductive activation remains poorly defined and controversial. The structurally related compound Apaziquone (5-aziridinyl-3-hydroxymethyl-1-methyl-2-[1H-indole-4,7-dione]prop-(3-en-a-ol), is a much better substrate for NQO1 than MMC and a good correlation exists between NQO1 activity and chemosensitivity in vitro under aerobic conditions. Under hypoxic conditions however, Apaziquone's properties are markedly different with little or no potentiation of Apaziquone toxicity observed in NQO1 rich cells. In NQO1 deficient cell lines however, large hypoxic cytotoxicity ratios have been reported. Therefore, Apaziquone has the potential to exploit the aerobic fraction of NQO1 rich tumors or the hypoxic fraction of NQO1 deficient tumors.

Apaziquone has been clinically evaluated but despite reports of three partial remissions in phase I clinical trials, no activity was seen against NSCLC, gastric, breast, pancreatic and colon cancers in subsequent phase II trials. See, e.g., Schellens, J. H. M., et al., Phase I and pharmacologic study of the novel indoloquinone bioreductive alkylating cytotoxic drug EO9, J. Natl. Cancer Inst. 86: 906-912 (1994); Dirix, L. Y., et al., EO9 phase II study in advanced breast, gastric, pancreatic and colorectal carcinoma by the early clinical studies group, Eur. J. Cancer 32A: 2019-2022 (1996). These findings are particularly disappointing in view of the preclinical studies together with reports that several tumor types have elevated NQO1 levels Hendriks. H. R., et al., EO9: A novel bioreductive alkylating indoloquinone with preferential solid tumor activity and lack of bone marrow toxicity in preclinical models, Eur. J. Cancer 29A: 897-906 (1993); Malkinson, A. M., et al., Elevated NQO1 activity and messenger RNA content in human non small cell lung carcinoma—Relationship to the response of lung tumor xenografts to MMC, Cancer Res. 52: 4752-4757 (1992); Smitskamp-Wilms, E., et al., NQO1 activity in normal and neoplastic human tissues: An indicator of sensitivity to bioreductive agents?, Br. J. Cancer 72: 917-921 (1995); Siegel, D., et al., Immunohistochemical detection of NAD(P)H:Quinone oxidoreductase in human lung and lung tumors. Clin. Cancer Res. 4: 2065-2070 (1998). Several possible explanations have been proposed to explain Apaziquone's lack of clinical efficacy. Recent studies have demonstrated that the failure of Apaziquone in the clinic may not be due to poor pharmacodynamic interactions but may be the result of poor drug delivery to tumors. Phillips, R. M., et al., Evaluation of a novel in vitro assay for assessing drug penetration into avascular regions of tumors, Br. J. Cancer 77: 2112-2119 (1998). The rapid plasma elimination of Apaziquone (tl/z=10 min in humans) in conjunction with poor penetration through multicell layers suggests that Apaziquone will not penetrate more than a few microns from a blood vessel within its pharmacokinetic lifespan (Schellens et al, 1994, Phillips et al, 1998). Intratumoural administration of Apaziquone to NQO1 rich and deficient tumors produced significant growth delays (although a distinction between damage to the aerobic or hypoxic fraction was not determined) suggesting that if Apaziquone can be delivered to tumors, therapeutic effects may be achieved. Cummings, J., et al., Pharmacological and biochemical determinants of the antitumour activity of the indoloquinone Apaziquone, Biochem. Pharmacol. 55: 253-260 (1998). While these undesirable characteristics are a serious setback for the treatment of systemic disease, paradoxically they may be advantageous for treating cancers which arise in a third compartment such as superficial bladder cancer. In this scenario, drug delivery is not problematical via the intravesical route and the penetration of Apaziquone into avascular tissue can be increased by maintenance of therapeutically relevant drug concentrations within the bladder (using a one hour instillation period for example).

While this method of instilling Apaziquone within the bladder may be useful, there still remains a need for drug delivery vehicles that are capable of delivering an effective amount of Apaziquone within the bladder. Furthermore, the use of bladder cancer treating pharmaceutical preparations with varying penetration profiles is needed to target superficial versus muscle invasive tumors. The present specification addresses these aspects of bladder cancer treatments.

SUMMARY OF THE INVENTION

Aspects of the present specification disclose pharmaceutical preparations for treating bladder cancer. The pharmaceutical preparations disclosed herein comprise an indoloquinone compound and a formulation vehicle. Exemplary indoloquinone compounds are bioreductive alkylating indoloquinones with anti-tumor effects such as, but not limited to, 3-hydroxymethyl-5-aziridinyl-1-1-methyl-2-[1H-indole-4,7-dione]propenol. Exemplary formulation vehicles include, without limitation, water, tert-butanol, alcohol, 2-hydroxypropyl-β-cyclodextrin, and combinations thereof. The pharmaceutical preparations disclosed herein may further comprise a bulking agent and/or a coating agent. An exemplary bulking agent is mannitol. Exemplary coating agents include, without limitation, propylene glycol, hydroxypropylcellulose, carboxymethylcellulose, chitosan hydrochloride, lectin, or polycarbophil.

Aspects of the present specification disclose lyophilized preparations for treating bladder cancer. The lyophilized preparations disclosed herein comprise an indoloquinone compound disclosed herein, a bulking agent disclosed herein, and optionally sodium bicarbonate.

Aspects of the present specification disclose reconstitution vehicles for treating bladder cancer. The reconstitution vehicles disclosed herein comprise a coating agent disclosed herein and pharmaceutically acceptable diluents. The reconstitution vehicles disclosed herein are used to reconstitute the lyophilized preparations disclosed herein.

Aspects of the present specification disclose method of treating bladder cancer by administering a therapeutic composition like the pharmaceutical preparations or reconstituted lyophilized preparations disclosed herein to a patient, where reducing a symptom associated with the bladder cancer is indicative of treating the cancer. Administration disclosed herein includes, without limitation, intravesical instillation, liposomal administration, or by intravascular administration.

Aspects of the present specification disclose methods of treating bladder cancer comprising determining the levels of at least one enzyme within a tumor and choosing a treatment based on the at least one enzyme level wherein the treatment comprises the administration of a quinone based bioreductive drug either alone or in combination with another treatment. The methods disclose herein further comprises determining the levels of hypoxia within a tumor and choosing a treatment based on the at least one enzyme level and the hypoxia level.

In particular embodiments according to the present invention, another treatment is radiotherapy and/or the administration of at least one chemotherapeutic agent.

DETAILED DESCRIPTION

Figure 1:
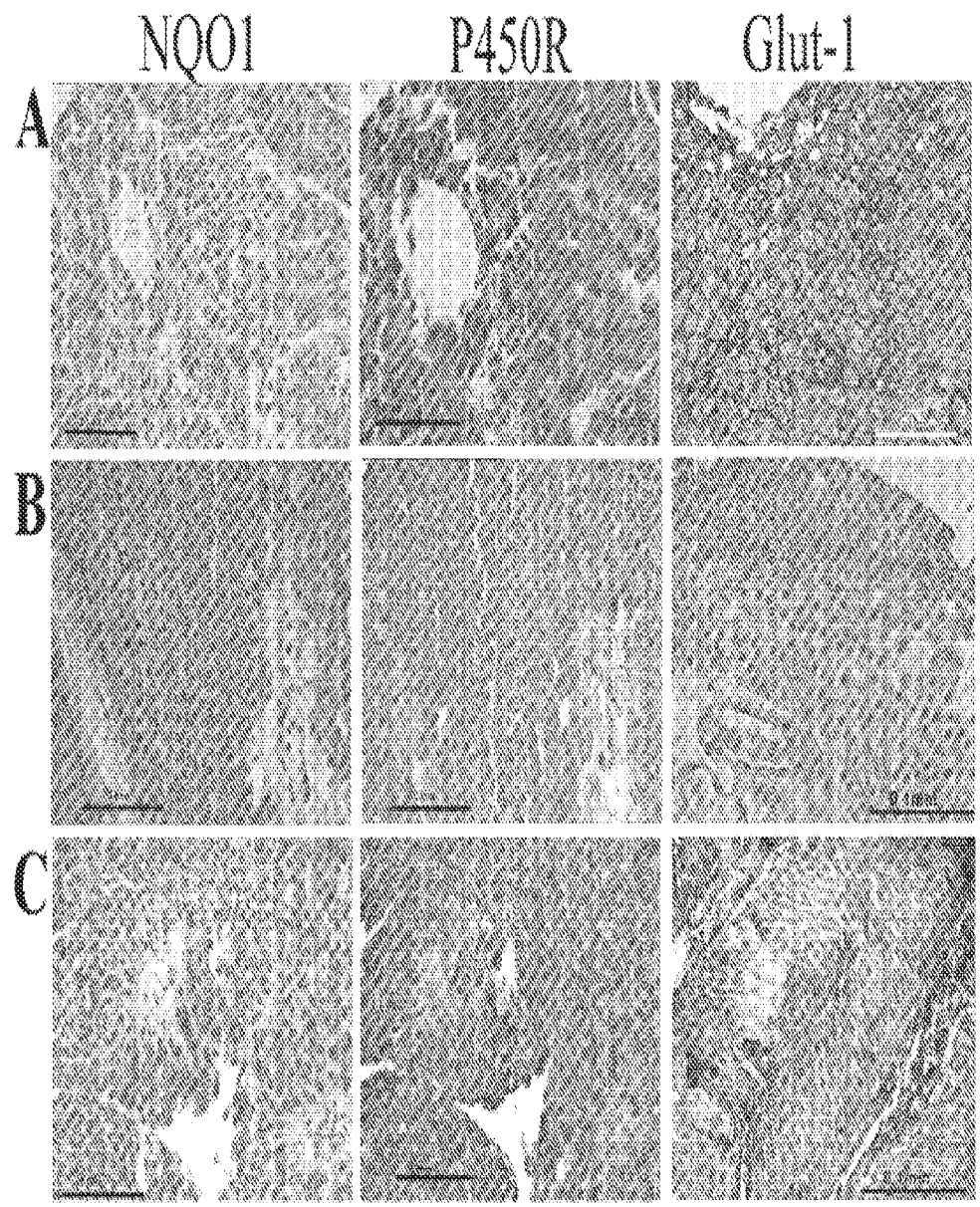
FIG. 1 shows the immunohistochemical analysis of NQO1, P450R and Glut-1 in three patients with transitional cell carcinoma of the bladder.

The present specification is directed to compositions and methods for treating bladder cancer. The disclosed compositions provide pharmaceutical preparations and reconstituted lyophilized preparations and therapeutic compositions with varying penetration profiles suited for treating different kinds of bladder cancer. For example, pharmaceutical preparations with lower penetration profiles would be beneficial to use when treating superficial bladder cancers because the drug would remain nearer the surface of the bladder where treatment is most needed. Conversely, pharmaceutical preparations with higher penetration profiles would be beneficial when treating more muscle invasive bladder cancers because the drug would penetrate to deeper layers of the bladder where treatment is most needed in those cases.

In one aspect the present specification discloses a composition comprising indoloquinone compound and a formulation vehicle. An indoloquinone compound is a bioreductive alkylating indoloquinone are cytostatic agents with anti-tumor effects. Indoloquinone compounds useful for the compositions and methods disclosed herein are described in, e.g., U.S. Pat. No. 5,079,257 incorporated herein in its entirety by reference for all it teaches related to indoloquinone synthesis, metabolism and therapeutic activity; and U.S. Pat. No. 6,894,071 incorporated herein in its entirety by reference for all it teaches related to Apaziquone formulations.

Indoloquinone compounds, include, without limitation, apaziquone. Apaziquone, also known as EO9 or NSC-382459, is a fully synthetic bioreductive alkylating indoloquinone. It is a pro-drug that generates cytotoxic species after enzymatic activation. The enzyme DTD (DT-diaphorase, also called NAD(P)H:quinone oxidoreductase-1, or NQO1) plays a prominent role in the activation of apaziquone under aerobic conditions. Apaziquone is also cytotoxic under hypoxic conditions, such as in cells with low DTD activity. The basic mechanism of activation of apaziquone is believed to be similar to that of other indoloquinones, involving reduction by cellular enzymes that transfer one or two electrons, forming semiquinone and hydroquinone, respectively. Oxidation of the semiquinone under aerobic conditions results in a redox cycle that can cause cell death by forming reactive oxygen species (ROS), resulting in DNA strand breaks. The semiquinone/hydroquinone can, particularly under hypoxic conditions, alkylate and crosslink DNA and other macromolecules, causing cell death.

The chemical name for Apaziquone is 5-(aziridin-1-yl)-3-(hydroxymethyl)-2-[(1E)-3-hydroxyprop-1-enyl]-1-methyl-1H-indole-4,7-dione, and this compound has the following structural formula:

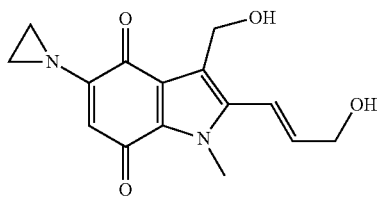 [SMILES: Cn1c(/C=C/CO)c(CO)c2c1C(=O)C=C(N1CC1)C2=O]

The formulation vehicles disclosed herein are solvents that improve the solubility and stability of an indoloquinone compound disclosed herein, such that the indoloquinone compound dissolves in the formulation vehicles without physical manipulation such as grinding. Because the compositions of the present invention are capable of dissolving greater amounts of an indoloquinone compound, additional flexibility with respect to dosage units is achieved. According to one embodiment, a content of 8.0 mg of Apaziquone per dosage unit is contemplated. In other embodiments, instillation doses range from approximately 0.5 mg to approximately 16 mg in a total volume of 40 mL.

In addition to improving the solubility of an indoloquinone compound, the formulation vehicles disclosed herein are good lyophilization vehicles. For example, the formulation vehicles disclosed herein minimize the time to lyophilize the compositions disclosed herein. Accordingly, in one embodiment, it is possible to lyophilize the compositions in less than approximately 4.5 days. Furthermore, the compositions disclosed herein are stable after undergoing lyophilization (see Table 4). It is believed that the formulation vehicles disclosed herein minimize the crystallization of an indoloquinone compound during the lyophilization process. Consequently, by reducing the amount of crystallization of an indoloquinone compound, a smaller volume of fluid is required to reconstitute a composition. As a result, a larger batch size can be achieved due to the reduced reconstitution volumes for the lyophilized composition.

According to one embodiment, a composition comprises Apaziquone and a formulation vehicle comprising tert-butanol. In aspects of this embodiment, the formulation vehicle comprises, e.g., 40% tert-butanol in water, 30% tert-butanol in water, 20% tert-butanol in water, or 10% tert-butanol in water. According to another embodiment, a composition comprises Apaziquone and a formulation vehicle comprises mixture of ethanol and water. In yet another embodiment, a composition comprises Apaziquone and a formulation vehicle is 2-hydroxypropyl-β-cyclodextrin. As those skilled in the art will appreciate, the amount of tert-butanol may be varied. The tert-butanol solution better dissolves Apaziquone as compared to water. By utilizing a tert-butanol formulation vehicle, solubility of Apaziquone is at least 9.5 mg/ml whereas the solubility of Apaziquone is approximately 0.2 mg/ml in water. Consequently, a smaller volume of the tert-butanol is required to dissolve a given amount of Apaziquone. Additionally, a greater amount of Apaziquone may be dissolved in a given solution. That is, the compositions disclosed herein will have a higher concentration of Apaziquone as compared to a solution where Apaziquone is dissolved in water.

In another aspect of the present specification, a composition disclosed herein comprises an indoloquinone compound, a formulation vehicle, and a bulking agent. Bulking agents include, e.g., lactose, maltitol, mannitol, xylitol, sorbitol, isomaltose, oligofructose and polydextrose. In one embodiment, lactose can be utilized as the bulking agent. As those skilled in the art will appreciate, it is contemplated that other bulking agents known or developed in the art may be utilized.

In another aspect of the present specification, a composition disclosed herein can be buffered. The composition can be buffered with any known or developed buffering agents including, without limitation, sodium carbonate, potassium carbonate, calcium hydroxide, sodium hydroxide, magnesium hydroxide, potassium hydroxide, sodium bicarbonate, magnesium oxide or calcium oxide. In some embodiments, the composition is buffered to a pH ranging from approximately 8 to approximately 8.5, approximately 8.5 to approximately 9, or approximately 9 to approximately 9.5. In other embodiments, the composition is buffered to a pH ranging from approximately 8 to approximately 9, approximately 8.5 to approximately 9.5, or approximately 8 to approximately 9.5.

The compositions disclosed herein can either be compounded to produce a pharmaceutical preparation stored either as an aqueous formulation or as a lyophilized preparation for subsequent reconstitution with a reconstitution vehicle disclosed herein.

Aspects of the present specification disclose a pharmaceutical preparation comprising an indoloquinone composition disclosed herein. In certain aspects, a pharmaceutical preparation disclosed herein further comprises a coating agent disclosed herein. The coating agents disclosed herein provide better adhesion of the composition to the bladder wall. Consequently, the preparation and, in particular, the indoloquinone compound contacts and may be able to penetrate the avascular tissue that comprises for a time sufficient to treat the bladder cancer. In one embodiment of the, the coating agent is propylene glycol. In other embodiments, the coating agent can be hydroxypropylcellulose, carboxymethylcellulose, chitosan hydrochloride, lectin, or polycarbophil.

In one embodiment, a pharmaceutical preparation disclosed herein comprises Apaziquone, propylene glycol, and water. Apaziquone concentrations can be present in a range from about 300 µM to about 400 µM. Propylene glycol concentrations can be present in a range from about 6% (v/v) to about 34% (v/v). In another embodiment, a pharmaceutical preparation comprises Apaziquone and propylene glycol, wherein the concentration of propylene glycol is a range of about 6% (v/v) to about 14% (v/v), about 16% (v/v) to about 24% (v/v), or about 26% (v/v) to about 34% (v/v). In yet another embodiment, a pharmaceutical preparation comprises Apaziquone and propylene glycol, wherein the concentration of propylene glycol is about 30% (v/v), about 20% (v/v), and about 10% (v/v). In still another embodiment, the preparation comprises about 347 µM Apaziquone. In another embodiment, a preparation comprises about 0.025 mg/mL to about 0.25 mg/mL Apaziquone. In yet another embodiment, a preparation comprises about 0.1 mg/mL Apaziquone.

A pharmaceutical preparation can further comprise sodium bicarbonate (NaHCO$_3$), disodium edetate (EDTA), and/or mannitol. Sodium bicarbonate can be present in a range from about 0 mg/mL to about 60 mg/mL. Mannitol can be present in a range from about 0 mg/mL to about 3.0 mg/mL. In one embodiment, a preparation comprises from about 1 mg/mL to about 20 mg/mL sodium bicarbonate. In one embodiment, a preparation comprises from about 2.5 mg/mL to about 10 mg/mL sodium bicarbonate. In another embodiment, a preparation comprises about 5.125 mg/mL sodium bicarbonate. In another embodiment, a preparation comprises about 0.35 mg/mL to about 3 mg/mL mannitol. In another embodiment the preparation comprises 1.25 mg/mL mannitol. In another embodiment, a preparation comprises about 0.625 mg/mL mannitol. In another embodiment, the preparation comprises about 5.125 mg/mL sodium bicarbonate, about 1.25 mg/mL mannitol and about 0.1 mg/mL Apaziquone in a solution comprising EDTA, propylene glycol, and water.

In another embodiment, a pharmaceutical preparation comprises Apaziquone, sodium bicarbonate and mannitol in a solution comprising propylene glycol, EDTA and water wherein the propylene glycol is present in a concentration range of about 6% (v/v) to about 14% (v/v), about 16% (v/v) to about 24% (v/v), or about 26% (v/v) to about 34% (v/v). In another embodiment, the propylene glycol is present in a concentration of about 10% (v/v), about 20% (v/v), or about 30% (v/v). In another embodiment, the preparation comprises about 300 µM to about 400 µM Apaziquone and about a 10% (v/v) propylene glycol. In yet another embodiment, the preparation comprises about 300 µM to about 400 µM Apaziquone and about 20% (v/v) propylene glycol. In a further embodiment, the preparation comprises about 300 µM to about 400 µM Apaziquone and about a 30% (v/v) propylene glycol. In yet another embodiment, the preparation comprises about 347 µM Apaziquone and about 30% (v/v) propylene glycol. These described embodiments can comprise about 0 mg/mL to about 60 mg/mL sodium bicarbonate and in particular embodiments will comprise about 1 mg/mL to about 20 mg/mL sodium bicarbonate, about 2.5 mg/mL to about 10 mg/mL sodium bicarbonate, or about 5.125 mg/mL sodium bicarbonate. These described embodiments can also comprise about 0.35 mg/mL to about 3.0 mg/mL mannitol and in particular embodiments will comprise about 0.625 mg/mL mannitol or about 1.25 mg/mL mannitol.

In one embodiment, a pharmaceutical preparation comprises about 347 µM Apaziquone, about 30% (v/v) propylene glycol, about 5.125 mg/mL sodium bicarbonate, about 1.25 mg/mL mannitol, about 0.1 mg/mL sodium edentate, and water. In another embodiment, a pharmaceutical preparation comprises about 347 µM Apaziquone, about 20% (v/v) propylene glycol, about 5.125 mg/mL sodium bicarbonate, about 1.25 mg/mL mannitol, about 0.1 mg/mL sodium edentate, and water. In another embodiment, a pharmaceutical preparation comprises about 347 µM Apaziquone, about 10% (v/v) propylene glycol, about 5.125 mg/mL sodium bicarbonate, about 1.25 mg/mL mannitol, about 0.1 mg/mL sodium edentate, and water.

Aspects of the present specification disclose a lyophilized preparation comprising an indoloquinone compound. As those skilled in the art will appreciate, the compositions can be lyophilized by those methods known or developed in the art. In one embodiment, a lyophilized formulation comprises about 1 mg/mL to about 8 mg of Apaziquone, about 2 mg to about 30 mg sodium bicarbonate, and about 10 to about 60 mg mannitol. In one embodiment, a lyophilized preparation comprises about 2 mg/mL to about 6 mg of Apaziquone, about 5 mg to about 15 mg sodium bicarbonate, and about 20 to about 40 mg mannitol. In another embodiment, a lyophilized preparation comprises about 4 mg of Apaziquone, about 5 mg sodium bicarbonate, and about 50 mg mannitol. Dosage amounts may vary due to several factors including, but not limited to, individual patient characteristics, type and/or stage of cancer, and/or the specific therapeutic composition administered.

A lyophilized preparation described herein may be reconstituted with any pharmaceutically acceptable diluent to produce a pharmaceutical preparation as disclosed herein. A reconstitution vehicle may comprise propylene glycol and water. A reconstitution vehicle disclosed herein dissolves the lyophilized disclosed herein and produces a stable solution for administration for up to 24 hours. Propylene glycol concentrations can be present in a range from about 0% (v/v) to about 60% (v/v). A reconstitution vehicle disclosed herein may further comprise sodium bicarbonate and disodium edetate. Sodium bicarbonate can be present in a range from about 0 mg/mL to about 60 mg/mL. EDTA concentrations can be present in a range from about 0 mg/mL to about 5 mg/mL. In one embodiment, a reconstitution vehicle disclosed herein comprises about 20% (v/v) to about 40% (v/v) propylene glycol, about 1 mg/mL to about 5 mg/mL sodium bicarbonate, about 0.01 mg/mL to about 1 mg/mL EDTA, and water. In one embodiment, a reconstitution vehicle comprises about 60% (v/v) propylene glycol, about 10 mg/mL sodium bicarbonate, about 0.2 mg/mL disodium edentate and water. In another embodiment, a reconstitution vehicle comprises about 40% (v/v) propylene glycol, about 5 mg/mL sodium bicarbonate, about 0.2 mg/mL disodium edentate and water. In yet another embodiment, a reconstitution vehicle comprises about 20% (v/v) propylene glycol, about 5 mg/mL sodium bicarbonate, about 0.2 mg/mL disodium edentate and water.

One type of pharmaceutical preparation is a reconstituted lyophilized preparation. Such a preparation is formed upon reconstitution of the lyophilized preparation disclosed herein with a reconstitution vehicle disclosed herein. The reconstituted lyophilized preparation can then be optionally diluted to a desired concentration and administered to a patient. In one embodiment, the final concentration of indoloquinone compound is in a range of about 300 μM to about 400 μM and the final concentration of propylene glycol is in a range from about 6% (v/v) to about 34% (v/v). In one embodiment, a reconstituted lyophilized preparation disclosed herein comprises about 347 μM Apaziquone, about 30% (v/v) propylene glycol, about 5.125 mg/mL sodium bicarbonate, about 1.25 mg/mL mannitol, about 0.1 mg/mL sodium edentate, and water.

Aspects of the present specification disclose methods of treating bladder cancer by administration of a therapeutic composition disclosed herein. A therapeutic composition includes a pharmaceutical preparation disclosed herein and a reconstituted lyophilized composition disclosed herein. These therapeutic compositions may be administered to a patient in need of treatment for cancer following TUR-BT. In one embodiment, a therapeutic composition may be administered to a patient via intravesical administration. In aspects of this embodiment, a therapeutic composition may be administered in a single instillation or a plurality of installations. In another aspect, the therapeutic composition may be administered in a single instillation given within six hours. In another aspect, the therapeutic composition may be administered in a single instillation given within six hours of TUR-BT. In another embodiment, a therapeutic composition may be administered to a patient via intravenously.

In one embodiment, a method of treating cancer includes administering a volume of a therapeutic composition disclosed herein of between about 2 mL and about 80 mL. In another embodiment, a method of treating cancer includes administering a volume of reconstituted lyophilized therapeutic composition of between about 30 mL and about 60 mL. In another embodiment, a method of treating cancer includes administering a volume of reconstituted lyophilized therapeutic composition of about 40 mL. Dosage volumes may vary due to several factors including, but not limited to, individual patient characteristics, type and/or stage of cancer, and/or the specific therapeutic composition administered.

In yet another embodiment, a composition disclosed herein can be delivered to the bladder wall by a liposome. According to one embodiment, the liposomes used are unilamellar or multilamellar and contain at least one cationic phospholipid such as stearylamine, 1,2-diacyl-3-trimethylammonium-propane (TAP) or 1,2-triacyl-3-dimethylammonium-propane (DAP). In another embodiment of the present invention, the surface liposomes may be coated with polyethylene glycol to prolong the circulating half-life of the liposomes. In yet another embodiment of the present invention, neutrally charged liposomes such as, but not limited to, phosphatidylcholine and cholesterol can also be used for liposomal entrapment of the compositions of the present invention. In another embodiment, the compositions of the present invention can be delivered to the bladder wall by a microsphere such as those known or developed in the art.

Significant differences in NQO1 expression were found between superficial and invasive tumors with low levels observed in muscle invasive tumors. In contrast, P450R and Glut-1 were expressed in all stages and grades of TCC although expression increased with tumor stage (particularly in the case of Glut-1). In addition, Glut-1 expression was significantly elevated in G3 tumors whereas low levels of NQO1 existed. These results demonstrated that marked differences in the expression of NQO1 and Glut-1 exist between superficial and invasive bladder TCC. These results have therapeutic implications for quinone based bioreductive drugs in that single agent therapy would be appropriate for superficial disease whereas for muscle invasive disease, combination therapy using quinones to target the hypoxic fraction and other modalities to eradicate the aerobic fraction would be desirable.

In another embodiment, the enzyme is selected from the group consisting of NAD(P)H:Quinone oxidoreductase-1 (NQO1) and NADPH cytochrome P450 reductase (P450R). In a particular embodiment, the enzyme is NQO1 and the treatment comprises the administration of a quinone based bioreductive drug alone. In another particular embodiment, the enzyme is NQO1 and the treatment comprises the administration of a quinone based bioreductive drug in combination with another treatment. In another particular the enzyme is P450R and the treatment comprises the administration of a quinone based bioreductive drug alone. In yet another particular the enzyme is P450R and the treatment comprises the administration of a quinone based bioreductive drug in combination with another treatment. In a further embodiment according to the present invention, the enzyme is NQO1 and P450R and the treatment comprises the administration of a quinone based bioreductive drug alone. In yet another embodiment, the enzyme is NQO1 and P450R and the treatment comprises the administration of a quinone based bioreductive drug in combination with another treatment.

Another embodiment includes a method of treating bladder cancer comprising choosing a treatment based on a measure selected from the group consisting of levels of NAD(P)H:Quinone oxidoreductase-1 (NQO1), levels of NADPH cytochrome P450 reductase (P450R), and levels of Glucose transporter-1 (Glut-1) wherein the treatment comprises the administration of a quinone based bioreductive drug either alone or in combination with another treatment. In various aspects of this particular embodiment: the measure can be NQO1 or P450R and the treatment comprises the administration of a quinone based bioreductive drug alone; the measure can be NQO1 or P450R and the treatment comprises the administration of a quinone based bioreductive drug in combination with another treatment; the measure can be NQO1 and P450R and the treatment comprises the administration of a quinone based bioreductive drug alone; the measure can be NQO1 and P450R and the treatment comprises the administration of a quinone based bioreductive drug in combination with another treatment; or the measure can be NQO1, P450R and Glut-1 and the treatment comprises the administration of a quinone based bioreductive drug alone or in combination with another treatment.

In one embodiment according to the present invention, the invention includes a method of treating invasive bladder cancer comprising determining the levels of NQO1 and Glut-1 within a tumor; selecting a combination treatment including a quinone based bioreductive drug in combination with another treatment based because said NQO1 level is lower and said Glut-1 level is higher than would be observed if said tumor was superficial.

In another embodiment according to the present invention, the invention includes a method of stratifying a patient for appropriate therapy for bladder cancer based on expression levels of NQO1 and Glut-1 within said patient's bladder tumor comprising: determining expression levels of NQO1 and Glut-1 within said patient's bladder tumor; and administrating a bioreductive drug as single agent therapy if said patient has superficial bladder cancer with high levels of NQO1 or administrating a combination therapy where a bioreductive drug is used in combination with radiation therapy or another chemotherapeutic agent if said patient has invasive bladder cancer with low NQO1 and high Glut-1 levels.

EXAMPLES

Example 1

NQ)1 Activity in Tumor and Normal Bladder Tissue

The following experiments were conducted to determine the activity of NQO1 in a series of human bladder tumors and normal bladder tissue by both enzymatic and immunohistochemical techniques.

In terms of bioreductive drug development, two of the critical factors which will ultimately determine selectivity are the enzymology of tumors and the presence of hypoxia (Workman, 1994). As outlined in the introduction, the presence or absence of NQO1 is central to the design of appropriate Apaziquone based therapeutic strategies aimed at targeting either the aerobic (NQO1 rich cells) or hypoxic fraction (NQO1 deficient tumors) of tumors. Workman (1994) has outlined a proposed mechanism for the different properties of Apaziquone under aerobic and hypoxic conditions based on the hypothesis that it is the semiquinone (product of one electron reduction) rather than the hydroquinone which is responsible for toxicity. In NQO1 deficient cells, the semiquinone produced as a result of one electron reductases would be relatively nontoxic as it would rapidly redox cycle back to the parent compound. Free radical species generated as a result of redox cycling would be detoxified by superoxide dismutase or catalase but under hypoxic conditions, the semiquinone would be relatively stable. If this were the major toxic species, then the activity of Apaziquone against cells with low NQO1 would be potentiated. In NQO1 rich cells however, the major product formed would be the hydroquinone. Aerobic toxicity could be generated as a result of the back oxidation of the hydroquinone to the semiquinone species or the parent quinone (Butler et al, 1996) resulting is free radical generation. Under hypoxic conditions however the hydroquinone will be more stable and if this is relatively nontoxic, then the activity of Apaziquone against NQO1 cells under hypoxia would not be potentiated. Whilst the mechanism of action of Apaziquone under aerobic and hypoxic conditions is complex, the biological data suggest that Apaziquone should target the aerobic fraction of NQO1 rich tumors or the hypoxic fraction of NQO1 deficient tumors (Workman, 1994).

Collection of tumor and normal bladder specimens. Ethical approval for tissue collection was obtained from the Local Research Ethical Committee (Bradford NHS Trust) and samples taken from patients following informed consent. A total of 17 paired cold pinch biopsies were taken from bladder tumors and macroscopically normal looking bladder mucosa at cystoscopy, immediately prior to formal transurethral resection of the tumor. Three specimens were taken from patients undergoing cystectomy and tumor and normal samples dissected by pathologists within one hour of surgical removal. Specimens were flash frozen in liquid nitrogen and transported for NQOI enzyme analysis. Further biopsies were taken of the normal bladder mucosa immediately adjacent to the previous biopsy site and sent at the end of the procedure, along with the resected tumor, in formalin for routine histological analysis. In this way bladder tumor and normal bladder urothelium enzymology could be directly correlated with the appropriate tissue histology in each patient. Immunohistochemistry was performed from the subsequently archived wax blocks prepared for histology.

Biochemical determination of NQOI activity. Cell cultures in exponential growth were trypsinised, washed twice with Hanks balanced salt solution (HBSS) and sonicated on ice ($3\times30$ sec bursts at 40% duty cycle and output setting 4 on a Semat 250 cell sonicator). NQO1 activity and protein concentration was determined as described below. Tissues were homogenised (10% w/v homogenate) in sucrose (0.25M) using a 1 ml tissue homogeniser (Fisher Scientific). Cytosolic fractions were prepared by centrifugation of the homogenate at 18,000 g for 4 min followed by further centrifugation of the supernatant at 110,000 g for 1 h at 4° C. in a Beckman Optima TL ultracentrifuge. Activity of NQO1 in the supernatant was determined spectrophotometrically (Beckman DU650 spectrophotometer) by measuring the dicumarol sensitive reduction of dichlorophenolindophenol (DCPIP, Sigma Aldrich, UK) at 600 nm (Traver et al, 1992). This assay has been extensively validated for use in measuring NQO1 activity in both tissue and cell homogenates and has been shown to be preferable to other assays for NQO1 activity (Hodnick and Sartorelli, 1997). Each reaction contained NADH (200 IzM), DCPIP (40/iM, Sigma Aldrich, UK), Dicumarol (20 uM, when required, Sigma Aldrich, UK), cytosolic fraction of tissues (50 p, l per assay) in a final volume of 1 ml Tris HCl buffer (50 mM, pH 7.4) containing bovine serum albumin (0.7 mg ml$^{-1}$, Sigma Aldrich, UK). Rates of DCPIP reduction were calculated from the initial linear part of the reaction curve (30 s) and results were expressed in terms of nmol DCPIP reduced/min/mg protein using a molar extinction coefficient of 21 mNT' cm$^{-1}$ for DCPIP. Protein concentration was determined using the Bradford assay (Bradford, 1976).

Immunohistochemistry. Polyclonal antibodies (raised in rabbits) to purified rat NQO1 were a gift from Professor Richard Knox (Enact Pharma Plc). Validation of the antibody for use in immunohistochemistry studies was performed by Western blot analysis using both purified human recombinant NQO1 and cell extracts derived from a panel of cell lines of human origin. These cell lines included H460 (human NSCLC), RT112 (human bladder carcinoma), HT-29 (human colon carcinoma), BE (human colon carcinoma), MT1 (human breast) and DLD-1 (human colon carcinoma). The BE cell line has been genotyped for the C609T polymorphic variant of NQOI and is a homozygous mutant (and therefore devoid of NQO1 enzyme activity) with respect to this polymorphism (Traver et al, 1992). Cells were washed in ice cold phosphate buffered saline and lysed by sonication (30 seconds on ice) in Tris HCl (50 mM, pH 7.5) containing 2 mM EGTA, 2 mM PMSF and 25 Ftg ml$^{-1}$ leupeptin. Protein concentration was estimated using the Bradford assay (Bradford, 1976) and a total of 12.5, ug of protein (in Lamelli sample loading buffer) applied to a 12% SDS-PAGE gel. Following electrophoretic transfer to nitrocellulose paper, membranes were blocked in TBS/Tween 20 (0.1%) containing 5% non-fat dry milk for 1 h at room temperature. Membranes were washed in TBS/Tween 20 (0.1%) prior to the addition of rabbit anti-rat NQO1 antibody (1:100 dilution) and incubated at room temperature for 1 h. Membranes were extensively washed in TBS/Tween 20 (0.1%) followed by the addition of anti-rabbit IgG horseradish peroxidase conjugated secondary antibody (1:5000 dilution in TBS/Tween 20). Proteins were visualised by ECL based chemiluminescence as described by the manufacturer (Amersham Pharmacia Biotech, Bucks, UK).

For immunohistochemical studies, all tissues (both tumor and normal bladder mucosa) were fixed in 10% formalin, processed routinely and embedded in paraffin wax. Two sections of each tissue block were placed on one slide, one section served as the test and the other as a negative control (no primary antibody). A total of 5 sections from each sample were stained for NQO1 (plus negative controls) and tumor and normal samples from a total of 17 patients were analysed. Sections (5, um) were dewaxed, rehydrated and incubated with primary antibody (1:400 dilution) for 4 hours. Sections were then washed and incubated with biotinylated mouse anti rabbit IgG for 30 min prior to immunoperoxidase staining using VECTASTAIN ABC reagents and DAB (Vector Laboratories Ltd, Peterborough, UK). Sections were counterstained with haematoxylin according to standard procedures.

TABLE 5

Tumor histology reports and NQO1 activity in paired samples of bladder tumor and normal bladder mucosa

| | | NQO1 Activity | | |
|---|---|---|---|---|
| Patient No. | Tumor histology | Tumor (nmol/min/mg) | Normal (nmol/min/mg) | Ratio tumor to normal tissue |
| 1 f, s, i, p | G2 pTa | 571.4 | <0.1 | 571.40 |
| 2 m, s, r | G3 pT2 | 273.3 | <0.1 | 273.30 |
| 3 f, s, i | G1 pTa | 107.80 | <0.1 | 107.80 |
| 4 m, e, i | G3 pT2/3 | 73.36 | <0.1 | 73.36 |
| 5 m, s, i | G3 pT4 (0' | 81.30 | 4.10 | 19.83 |
| 6 [h] | G2 PT1 | 309.50 | 25.20 | 12.10 |
| 7 m, n, r, o | G3 pT2 | 10.00 | <0.1 | 10.00 |
| 8 f n, i | G3 pT2 | 9.80 | <0.1 | 9.80 |
| 9 m, n, i | G2 pT2 | 4.40 | <0.1 | 4.40 |
| 10 m, s, c | G3 pT2 | 34.01 | 8.50 | 4.00 |
| 11 [m,s] | G1 pTa | 69.76 | 22.20 | 3.14 |
| 12 ,, n | G1 pTa | 42.16 | 15.30 | 2.73 |
| 13 m, n, i | G3 pT2 | 179.6 | 72.12 | 2.49 |
| 14 m, e, i | G2/G3 T4 (C) | 89.70 | 63.30 | 1.41 |
| 15 m, n, r | G3 pT2 | 0.40 | <0.1 | 0.40 |
| 16 m, e, c, o | G3 PT3 (C) | 21.60 | 61.70 | 0.35 |
| 17 f n, i | G2 PTI | 58.40 | 190.90 | 0.30 |
| 18 m, e, o | G2 PTI | <0.1 | <0.1 | 0 |
| 19 f n, i | G2 PT I. | <0.1 | <0.1 | 0 |
| 20 m, e, c, r | G2 pTO | <0.1 | <0.1 | 0 |

[m]Male, [f]Female, [s] Smoker, 'Non-smoker, [e]Ex-smoker, [o] Intravesical chemotherapy prior to specimen collection, [r] Radiotherapy prior to specimen collection,' First presentation, P Previous malignancy other than bladder, [h]No medical history available, [o] Possible occupational carcinogen exposure (i.e., dye industry worker). (C) denotes cystectomy specimens. In all cases, protein levels following preparation of the cytosolic fraction were greater than 0.1 mg/ml.

Analysis of NQO1 activity in tumor and normal bladder tissues has clearly identified patients whose tumors are either NQO1 rich or NQO1 deficient (Table 1). Within the subset of NQO1 rich tumors, enzyme activity is elevated relative to the normal bladder urothelium. Immunohistochemical studies confirm these biochemical measurements with staining confined to tumor cells as opposed to normal stromal cells. Within normal bladder tissues, NQO1 staining was absent from the urothelial lining of the bladder and the urethra. Faint staining of the superficial layers of the ureter was observed although the underlying basal layers of the ureter were negatively stained. Similarly, faint staining of the smooth muscle layers of the bladder, ureter and urethra were also observed. These studies suggest that a proportion of patients with bladder tumors (at various grades and stages of the disease) exhibit a significant differential in terms of NQO1 activity which could potentially be exploited by Apaziquone based therapies directed against the aerobic fraction of tumor cells. With regards to the ability of Apaziquone to selectively kill hypoxic NQO1 deficient cells, a subset of patients also exist whose tumors are devoid of NQO1 activity (Table 1). It is not known whether or not bladder tumors contain regions of low oxygen tension and further studies are required using hypoxia markers such as pimonidazole (Kennedy et al, 1997) to address this issue and to establish the relationship between NQO1 activity and hypoxia in tumors.

Example 2

Intravesical Administration

The following experiments evaluate strategies for reducing possible system toxicity arising from intravesical therapy based upon the fact that the aerobic activity of Apaziquone against cell lines is enhanced under mild acidic conditions. Administration of Apaziquone in an acidic vehicle would result in greater activity within the bladder and any drug absorbed into the blood stream would become relatively inactive due to the rise in extracellular pH. The following experiments also determine the role of NQO1 in the activation of Apaziquone under acidic conditions.

Cell culture and chemosensitivity studies. Apaziquone was a gift from NDDO Oncology, Amsterdam and MMC was obtained from the Department of Pharmacy, St Lukes Hospital, Bradford. H460 (human NSCLC) cell line was obtained from the American Type Culture Collection (ATCC). HT-29 (human colon carcinoma), RT112/83 (human bladder carcinoma epithelial), EJ138 (human bladder carcinoma) and T24/83 (human bladder transitional cell carcinoma) cell lines were obtained from the European Collection of Animal Cell Cultures (ECACC). A2780 (human ovarian carcinoma) and BE (human colon carcinoma) cells were gifts from Dr T Ward (Paterson Institute, Manchester, UK). All cell lines were maintained as monolayer cultures in RPNII 1640 culture medium supplemented with fetal calf serum (10%), sodium pyruvate (2 mM), L-glutamine (2 mM), penicillin/streptomycin (50 IU/ml/50 jug/ml) and buffered with HEPES (25 mK. All cell culture materials were purchased from Gibco BRL (Paisley, UK). Cells were exposed to MMC or Apaziquone at a range of doses for one hour and chemosensitivity was assessed following a five day recovery period using the MTT assay, details of which have been described elsewhere (Phillips et al, 1992). The pH of the medium used during drug exposure was adjusted using small aliquots of concentrated HCl (40, A conc HCl [10.5M] to 20 ml medium gives a pH of 6.0). Calibration curves were conducted over a broad range of pH values in culture medium (pH 3.5 to 11) and the stability of the pH conditions monitored over a one hour incubation period at 37° C. At all pH values, no significant changes in the pH of the medium was observed over the one hour drug exposure period (data not presented).

HT-29 multicell spheroids were prepared by seeding $5 \times 10^5$ cells into T25 flasks which had been based coated with agar (1% w/v) and incubated for 24 h at 37° C. Immature spheroids were then transferred to a spinner flask (Techne) containing 250 ml of RPMI 1640 growth medium and spheroids were kept in suspension by stirring at 50 rpm. When spheroids reached a diameter of approximately 500 Am, they were harvested for chemosensitivity studies. Multicell spheroids were exposed to a range of Apaziquone concentrations at pHe 6.0 and 7.4 for one hour at 37° C. Following drug incubation, spheroids were washed twice in HBSS prior to dissagregation into single cells using trypsin EDTA. Disaggregated spheroids were then washed in HBSS and then plated into 96 well plates ($1\times10^3$ cells per well) and incubated at 37° C. for four days. Chemosensitivity was assessed using the NM assay as described elsewhere (Phillips et al, 1992).

The role of NQO1 in the activation of Apaziquone at pHe values of 7.4 and 6.0 was evaluated using the NQO1 inhibitor Flavone Acetic Acid (FAA), details of which are described elsewhere (Phillips, 1999). FAA is a competitive inhibitor of NQO1 with respect to NADH and at a final concentration of 2 mM, inhibition of NQO1 is >95% whereas the activity of cytochrome P450 reductase and cytochrome b5 reductase is not substantially altered (<5% inhibition). Briefly, H460 cells (NQO1 rich) were plated into 96 well plates at a density of $2\times10^3$ cells per well. Following an overnight incubation at 37° C., medium was replaced with fresh medium (pH 7.4) containing a non-toxic concentration of FAA (2 mM) and incubated for one hour at 37° C. Medium was then replaced with fresh medium containing Apaziquone (range of drug concentrations) and FAA (2 mM) at either pHe 7.4 or 6.0. Following a further one hour incubation at 37° C., cells were washed twice with HBSS and incubated at 37° C. in growth medium for five days. Chemosensitivity was determined by the NM assay as described above and results were expressed in terms of $IC_{50}$ values, selectivity ratios ($IC_{So}$ at pHe 7.4/IC50 at pHe 6.0) and protection ratios (ICSO FAA/Apaziquone combinations/IC50 for Apaziquone alone).

Substrate specificity. The influence of acidic pHe on substrate specificity for purified human NQO1 was determined as described previously (Phillips 1996, Walton et al, 1991). NQO1 mediated reduction of the quinone to the hydroquinone species is difficult to detect by conventional assays thereby necessitating the use of a reporter signal generating step. In this assay, the hydroquinone acts as an intermediate electron acceptor which subsequently reduces cytochrome c which can readily be detected spectrophotometrically. Recombinant human NQO1 was derived from $E.$ $coli$ transformed with the pKK233-2 expression plasmid containing the full length cDNA sequence for human NQO1 isolated from the (Beall et al, 1994). Following IPTG induction, NQO1 was purified by cybacron blue affinity chromatography, details of which are described elsewhere (Phillips, 1996). The purified protein had a molecular weight of approximately 31 kDa and a specific activity of 139/Amol DCPIP reduced/min/mg protein (Phillips, 1996). Reduction of Apaziquone by recombinant human NQO1 was determined at pH 6.0 and 7.4 by measuring the rate of reduction of cytochrome c was measured at 550 nm on a Beckman DU 650 spectrophotometer according to previously published methods (Phillips, 1996). Results were expressed in terms of, μmol cytochrome c reduced/min/mg protein using a molar extinction coefficient of 21.1 $mM^{-1}$ $cm^{-1}$ for cytochrome c.

Measurement of intracellular pH. Intracellular pH was determined using the fluorescent pH indicator BCECF (2,7-bis-(2-carboxy-ethyl)-5-(and-6) carboxyfluorescein (Molecular Probes, Eugene, USA) according to manufacturers instructions. Confluent flasks of cells were washed with HBSS to remove any traces of serum containing RPMI medium and then incubated with the esterified form of BCECF (BCECF-AM) at a concentration of 2 [tM in HBSS for one hour at 37° C. The non-denaturing detergent Pluronic was added to the probe to aid dispersion. Cells were then washed to remove all traces of BCECF-AM and then trypsinized before being suspended in serum-free/phenol red-free RPM1 medium (Gibco BRL, Paisley, UK) at a concentration of $10^6$ cells per ml at pH 6 for one hour. Fluorescence measurement was determined in a Perkin-Elmer fluorescence spectrophotometer in UV grade disposable 4 ml cuvettes (Fischer Scientific) with excitation wavelengths 500 nm and 450 nm (excitation bandpass slit of I0 nm) and emission wavelength fixed at 530 nm (emission bandpass slit of 2.5 nm). These were determined to be optimal settings for the machine and system under study. An in-situ calibration was performed for every pHi determination with a range of six pH's from 4 to 9 using the ionophore nigericin at a concentration of 22.8 p,M to equilibrate pHe with pHi. Calculation of the ratio of fluorescence at 500 nm/450 nm was calculated after subtraction of background fluorescence from blanks at each pH (serum free, phenol red free RPMI without cells).

Activity of NQO1 in tumor and normal bladder specimens. The biochemical activity of NQO1 in paired samples of tumor (grade/stage ranging from G2 pTa to G2/G3 T4) and normal bladder mucosa (with three cystectomy specimens) taken from a series of 20 patients is presented in Table 1. Within the tumor specimens, a broad range of NQO1 activity existed ranging from 571.4 nmoUmin/mg to undetectable (<0.1 nmol/min/mg). In histologically normal bladder mucosa specimens, NQO1 activity ranged from 190.9 to <0.1 nmoUmin/mg. In the majority of patients NQO1 activity in the tumor was greater than in the normal bladder mucosa. Tumor grade and stage did not correlate with NQO1 activity (Table 1).

Validation of NQO1 antibody and immunohistochemical localization of NQO1. Western blot analysis demonstrates that polyclonal anti rat NQO1 antibody cross reacts with human NQO1 with a single band at approximately 31 kDa observed for both cell extracts and purified human NQO1. Titration of purified NQO 1 results in a decrease in band intensity and in cell extracts, band intensity was qualitatively consistent with NQO1 enzyme activity. In addition, the antibody does not detect NQO1 in the BE cell line which is devoid of NQO1 activity as a result of the C609T polymorphism. No non-specific bands were observed on Western blots. Superficial and invasive tumors with high to intermediate levels of NQO1 as determined by biochemical assays (patient numbers 1, 4 and 5 in Table 1) clearly stained positive for NQO1. Staining was confined to the cytoplasm of tumor cells with little or no staining of stromal cells.

In other tumors with intermediate or low levels of NQOI activity, staining was heterogeneous with pockets of cells containing high levels of NQO1 protein. Normal bladder wall sections were obtained from a patient who underwent cystectomy (G3pT4 bladder tumor), ureter and urethra were obtained from another patient who underwent cystectomy (G3 pT3a bladder tumor). In the bladder wall, no NQO1 staining was observed in the urothelium although slight staining was present in smooth muscle layers. The urethra was negative although cells on the luminal surface of the ureter were positively stained. The basal layers of the ureter lining were however negatively stained. No evidence of invasive malignancy or in situ carcinoma were observed in the ureter and urethra or in the section of bladder wall presented. In 16 other normal bladder biopsy and cystectomy specimens, no positive staining of the urothelium was observed.

Influence of pH on substrate specificity and chemosensitivity. The ability of Apaziquone to serve as a substrate for NQO1 was not influenced by pH with specific activities of 21.10±2.3 and 21.30±1.5 pmol cytochrome c reduced/min/mg protein at pH 7.4 and 6.0 respectively. The response of a panel of cell lines with a range of NQO1 activity (<1.0 to 1,898±276 nmol/min/mg) to Apaziquone and MMC at pHe values of 7.4 and 6.0 is presented in Table 2. At pHe=7.4, a good correlation existed between NQO1 activity and chemosensitivity to Apaziquone. In the case of MMC (Table 2), a relationship between NQO1 and chemosensitivity was apparent (at pHe 7.4) although this relationship was not as prominent as shown by Apaziquone with a narrow range of IC50 values (range 0.9 to 7.0 ttM) observed in cell lines which cover a broad range of NQO1 activity (ranging from <1.0 to 1,898 nmol/min/mg). Both MMC and Apaziquone are preferentially more toxic to cells at pHe values of 6.0 although much greater potentiation of Apaziquone activity is seen with SR values (SR=selectivity ratio defined as $IC_{50}$ pHe 7.4/IC50 pHe 6.0) ranging from 3.92 to 17.21 for Apaziquone compared with 1.02 to 4.50 for MMC (Table 2). The activity of Apaziquone was enhanced in both NQO1 rich and deficient cell lines when pHe was reduced to 6.0 and the relationship between NQO1 and chemosensitivity remained good when cells were exposed to Apaziquone under acidic conditions. No cell kill was observed in control cultures when the pHe was decreased to 6.0 (in the absence of drug) as determined by the MTT assay. The response of H460 cells to Apaziquone at pHe values of 7.4 and 6.0 in the presence and absence of FAA (2 mM) is presented in Table 3. At both pHe values, the response of H460 cells to Apaziquone was reduced in the presence of FAA. Protection ratios defined as the IC50 for Apaziquone plus FAA divided by the IC50 value for Apaziquone alone were similar for cells under acidic and physiological pHe values (14.63 and 13.95 respectively, Table 3). Selectivity ratios defined as the IC50 at pHe 7.4 divided by the IC50 at pHe 6.0 in the presence and absence of FAA were also similar with SR values of 6.31 and 6.02 for Apaziquone alone and Apaziquone plus FAA respectively (Table 3). The response of HT-29 multicell spheroids to Apaziquone demonstrate that spheroids exposed to Apaziquone at pHe 6.0 were significantly more responsive than at pHe 7.4 with IC50 values of 9.89±0.89 and 24.24±3.29 AM respectively. Spheroids were significantly less responsive to Apaziquone than the same cells exposed to Apaziquone as monolayers at both pHe values with ratios of IC50 values for spheroids to monolayers of 202 and 341 at pHe values of 7.4 and 6.0 respectively.

Influence of acidic pHe conditions on pHi. PM values following a one hour incubation at pHe 6.0 were 6.44±0.04, 6.51±0.02 and 6.42±0.05 in A549, RT112/83 and A2780 cells respectively. Addition of the ionophore nigericin (after a one hour incubation at pHe 6.0) resulted in the equilibration of pHe and p11i.

Whilst biochemical and immunohistochemical studies demonstrate that a subset of patients exist which have the appropriate tumor enzymology to activate Apaziquone (under aerobic conditions), intravesical chemotherapy can result in systemic toxicity due to the drug entering the blood supply. This study has also evaluated a potential strategy for minimizing any risk of systemic toxicity based upon the hypothesis that administration of Apaziquone in an acidic vehicle would enhance the potency of Apaziquone (Phillips et al, 1992) within the bladder and that any drug reaching the blood stream would become relatively inactive due to a rise in pHe. Selectivity for aerobic cells would still be determined by NQO1 activity and therefore it is essential to determine the role that NQO1 plays in the activation of Apaziquone under acidic pHe conditions. In a panel of cell lines with a broad spectrum of NQO1 activity, reducing the pHe to 6.0 enhances the potency of Apaziquone under aerobic conditions in all cases (with SR values ranging from 3.92 to 17.21, Table 2). In the case of MMC, potency is also enhanced at low pHe values although the magnitude of the pH dependent increase in toxicity is reduced (SR values ranging from 1.02 to 4.50, Table 2) compared with Apaziquone. With respect to MMC, one explanation for increased activity under acidic conditions has been attributed to the fact that MMC becomes a substrate for NQO1 under acidic conditions (Pan et al, 1993, Siegel et al, 1993). This is not the case with Apaziquone as rates of reduction of Apaziquone by purified human NQO1 are not influenced by pH (21.10±2.30 and 21.30±1.50 limol cytochrome c reduced/min/mg protein at pH 7.4 and 6.0 respectively). Recent studies have demonstrated that the activity of Apaziquone is enhanced under acidic conditions (pHe=6.5) but only when the intracellular pH is reduced (plli=6.5) by co-incubation with nigericin (Kuin et al, 1999). The results of this study are in agreement with this finding as pHi becomes acidic (pHi values range from 6.42±0.05 to 6.51±0.02 depending on the cell line) when cells are cultured under pHe 6.0 conditions.

In the panel of cell lines used in this study, a good correlation exists between NQO1 activity and chemosensitivity at both pHe values of 7.4 and 6.0. A strong relationship between

TABLE 2

Relationship between NQO1 activity and chemosensitivity to Apaziquone and MMC under physiological and acidic pHe conditions.

| Cell line | Drug | NQO1 (nmol/min/mg) | IC50 pHe 7.4 (nM) | IC50 pHe 6.0 (nM) | SR* |
|---|---|---|---|---|---|
| H460 | Apaziquone | 1652 ± 142 | 60 ± 10 | 9.5 ± 2 | 6.31 |
| HT-29 | Apaziquone | 688 ± 52 | 120 ± 53 | 29 ± 10 | 4.13 |
| T24/83 | Apaziquone | 285 ± 28 | 290 ± 65 | 60 ± 18 | 4.83 |
| A2780 | Apaziquone | 159 ± 33 | 200 ± 50 | 51 ± 14 | 3.92 |
| EJ138 | Apaziquone | 83 ± 14 | 310 ± 95 | 39 ± 7 | 7.94 |
| RT112 | Apaziquone | 30 ± 3 | 1050 ± 75 | 61 ± 13 | 17.21 |
| BE | Apaziquone | <0.1 | 5300 ± 169 | 1300 ± 75– | 4.07 |
| H460 | MMC | 1652 ± 142 | 900 ± 200 | 220 ± 130 | 4.50 |
| HT-29 | MMC | 688 ± 52 | 1050 ± 210 | 500 ± 240 | 2.10 |
| T24/83 | MMC | 285 ± 28 | 2150 ± 93 | 2100 ± 800 | 1.02 |
| A2780 | MMC | 159 ± 33 | 2400 ± 340 | 1400 ± 130 | 1.71 |
| EJ138 | MMC | 83 ± 14 | 1600 ± 200 | 1400 ± 250 | 1.14 |
| RT112 | MMC | 30 ± 3 | 3350 ± 250 | 2000 ± 500 | 1.67 |
| BE | MMC | <0.1 | 7000 ± 192 | 4400 ± 215 | 1.59 |

All results presented are the mean of 3 independent experiments (SD values omitted in the interests of presentation).
*SR (selectivity ratio) = IC5o at pH 7.4/IC5o at pH 6.0

NQO1 activity and response under aerobic conditions (at pHe 7.4) has been established previously by several groups (Robertson et al, 1994, Fitzsimmons et al, 1996, Smitkamp-Wilms et al, 1994) and there is clear evidence that NQO1 plays a central role in the mechanism of action of Apaziquone under aerobic conditions (Workman, 1994). The good correlation between NQO1 activity and response at pHe 6.0, in conjunction with the fact that Apaziquone is still a good substrate for NQO1 at pH 6.0, suggests that NQO1 plays a significant role in Apaziquone's mechanism of action at acidic pHe values under aerobic conditions. It is of interest to note however that the activity of Apaziquone against BE cells (which are devoid of NQO1 activity as a result of the C609T polymorphism, Traver et al, 1992) is also enhanced under acidic pHe conditions (Table 2). This suggests that there is a NQO1 independent mechanism for the increased activity of Apaziquone under acidic conditions. This is confirmed by the use of the NQO1 inhibitor FAA where the 'protection ratios' (defined as the ratio of $IC_{50}$ values for Apaziquone plus FAA divided by the ICSo values for Apaziquone) are similar at both pHe 7.4 and 6.0 (13.95 and 14.63 respectively, Table 3). If NQO1 played a central role in the activation of Apaziquone at pHe 6.0, then the protection ratio at pHe 6.0 would be significantly greater than the protection ratio at pHe 7.4. The mechanism behind the NQO1 independent activation of Apaziquone is unclear although it is a well known fact that the reactivity of aziridine ring structures is enhanced by protonation resulting in ring opening to the aziridinium ion which is a potent alkylating species (Mossoba et al, 1985, Gutierrez, 1989). Alternatively, Apaziquone is a substrate for other one electron reductases (Maliepaard et al, 1995, Saunders et al, 2000) and further studies designed to evaluate whether Apaziquone's metabolism by these enzymes is pH dependent needs to be determined. The potency of Apaziquone can be enhanced further by reducing pHe below 6.0 (Phillips et al, 1992) but these conditions are unlikely to provide significant clinical benefits as Apaziquone becomes progressively more unstable when pH is reduced to 5.5 (t'/s=37 min). From a pharmacological standpoint, administration of Apaziquone in a vehicle at pH 6.0 would appear desirable. Not only would this result in significant enhancement of Apaziquone activity but also the stability of Apaziquone would be sufficient (tlh=2.5 h) to maintain drug exposure parameters at a therapeutic level.

TABLE 3

Response of H460 cells to Apaziquone in the presence or absence of FAA (2mm) at pHe values of 7.4 and 6.0.

| Drug | pHe | ICso (nM) | SR* | PR** |
|---|---|---|---|---|
| Apaziquone | 7.4 | 60.0 ± 8.1 | — | — |
| Apaziquone | 6.0 | 9.5 ± 2.6 | 6.31 | — |
| Apaziquone/FAA | 7.4 | 837 ± 45 | — | 13.95 |
| Apaziquone/FAA | 6.0– | 139 ± 27 | 6.02 | 14.63 |

*SR = Selectivity Ratio defined as the ratio of ICSo values at pHe = 7.4 divided by the $IC_{50}$ at pHe = 6.0.
**PIf = Protection ratio defined as the ratio of $IC5_o$ values for Apaziquone plus FAA divided by the ICSo values for Apaziquone alone.
All values represent the mean ± standard deviation for three independent experiments.

With regards to the activity of Apaziquone against three dimensional culture models in vitro, this study has demonstrated that reducing the pHe to 6.0 enhances the potency of Apaziquone against multicell spheroids although the magnitude of this effect is reduced compared with monolayer cultures. It is not known whether or not reduction in pHe results in greater cell kill throughout the spheroid or if it is confined to the surface of the spheroid exposed to medium. In comparison with MMC, previous studies using histocultures exposed to MMC demonstrated that no difference in toxicity exists between physiological and acidic pHe conditions (Yen et al, 1996). The pH dependent increase in Apaziquone toxicity against spheroids suggests that manipulation of pHe may not only be of use in treating a multilayered solid bladder tumor but may offer an advantage over MMC. It should however be stated that multicell spheroids are significantly less responsive to Apaziquone than mono] layers, presumably because of the poor penetration properties of Apaziquone through avascular tissue (Phillips et al, 1998). Apaziquone can nevertheless kill >90% of cells in spheroids suggesting that a higher doses at least, the penetration of Apaziquone is sufficient to eradicate cells which reside some distance away from the surface of the spheroid.

In conclusion, the results of this study have demonstrated that within a population of patients with bladder tumors at various stages and grades of the disease, there exists a great heterogeneity regarding the expression of NQO1. The majority of patients have tumors possessing elevated levels of NQO 1 while a small subset of patients appear to be devoid of NQO1 activity. The heterogeneous nature of NQO1 activity described here is consistent with several other studies in various tumor types (Malkinson et al, 1992, Smitkamp-Wilms et al, 1995, Siegel et al, 1998). These findings reinforce the view that 'enzyme profiling' of individual patients could be valuable prior to therapeutic intervention with bioreductive drugs (Workman, 1994). This is to our knowledge the first study to characterize NQO1 activity and cellular localization in bladder tumors and provide strong evidence to support the evaluation of Apaziquone against superficial and locally invasive bladder tumors. This study has clearly demonstrated that under aerobic conditions, Apaziquone is much more potent under acid conditions (pH6.0) than at physiological pH (pH7.4). The mechanism for this increased Apaziquone potency appears to be NQO1 independent and whilst this will not improve (or reduce) selectivity, it may prove beneficial in terms of reducing the therapeutically effective dose of Apaziquone. Dose reduction in conjunction with the fact that a reduction in the potency of Apaziquone due to the increased pHe in the blood stream suggests that systemic toxicity arising from the intravesical administration of Apaziquone would be low. In addition, this study shows that under physiological conditions the activity of Apaziquone is much lower in tissues with "normal" expression of NQO1 compared to "high" NQO1 expressing tissues (i.e. the tumors). The results of this study provide strong evidence in support of the proposal that intravesical administration of Apaziquone may have activity against bladder tumors.

TABLE 4

Neoquin 8 mg/vial lyophilised product

| Storage | Test item | Time (months) | | | | |
|---|---|---|---|---|---|---|
| | | 0 | 1 | 2 | 3 | 6 |
| 5° C. | content* | 102.7 ± 1.2 | na | na | 103.8 ± 0.8 | 100.6 ± 0.6 |
| | purity** | 99.9 ± 0.008 | na | na | 99.5 ± 0.03 | 99.6 ± 0.03 |
| | residual moisture*** | 6.0% | na | na | 7.0% | 6.3% |
| | pH after reconstitution**** | 9.5 | na | na | na | 9.4 |
| 25° C. 60% RH | content | 102.7 ± 1.2 | 103.4 ± 0.7 | 102.1 ± 0.2 | 102.6 ± 1.3 | 97.4 ± 1.0 |
| | purity | 99.9 ± 0.008 | 99.9 ± 0.05 | 99.9 ± 0.01 | 99.2 ± 0.07 | 98.7 ± 0.2 |
| | residual moisture | 6.0% | na | na | 5.9% | 5.9% |
| | pH after reconstitution**** | 9.5 | na | na | na | 9.4 |
| 40° C. 75% RH | content | 102.7 ± 1.2 | 102.3 ± 1.1 | 100.4 ± 1.3 | 101.3 ± 0.2 | 86.4 ± 2.0 |
| | purity | 99.9 ± 0.008 | 99.8 ± 0.01 | 99.7 ± 0.04 | 98.4 ± 0.07 | 97.5 ± 0.2 |
| | residual moisture | 6.0% | na | na | 6.2% | 6.3% |
| | pH after reconstitution**** | 9.5 | na | na | na | 9.5 |

*content as % of labelled content n = 3
**purity as chromatographic purity n = 3

Example 3

Relationship Between Markers and Tumor Stage and Grade

Quinone based bioreductive drugs are pro-drugs that generate cytotoxic species after enzymatic activation. The enzyme NAD(P)H:quinone oxidoreductase-1 (NQO1; also called DT-diaphorase (DTD)), a two electron reductase enzyme, plays a prominent role in the activation of quinone based bioreductive drugs under aerobic conditions. Quinone based bioreductive drugs are also cytotoxic under hypoxic conditions including cells with low NQO1 activity. One electron reducing enzymes such as Cytochrome P450 reductase may play a more prominent role in the activation of quinine based bioreductive drugs under hypoxic conditions. Based on the foregoing, the levels of these reductases and hypoxic conditions can indicate the appropriateness of different cancer therapies including the appropriateness of using various quinone based bioreductive drugs. The present invention thus evaluated levels of the described reductases and hypoxic condition in various grade and stage TCC.

Formalin-fixed, paraffin-embedded specimens of human bladder transitional cell carcinomas (n=52) were used for this study after first obtaining consent from the local research and ethics committee (LREC) according to Medical Research Council regulations. All patient details were anonymised to ensure confidentiality and all experiments were performed in accordance with guidelines laid down by the LREC. The tumors used for the study were representative of all grades (11 Grade 1; 26 Grade 2; 15 Grade 3) of both superficial (19 pTa; 19 pT1) and muscle-invasive (14≥pT2) stages of human bladder TCC. All tumor blocks were used for construction of tissue microarrays (TMAs) and subsequent immunohistochemical analysis.

Tissue microarray constructions (TMAs) were constructed from the paraffin embedded blocks to represent the various grades (G1-G3) and the various stages (pTa, pT1, ≥pT2) of human bladder TCC. Tissue microarray construction (TMA) was achieved using a Beecher Instruments microarrayer (Silver Spring, Md., USA) using a modified method of Bubendorf et al. which is incorporated by reference herein. Briefly, sections of each paraffin embedded donor block were stained using hematoxylin and eosin (H&E), examined by microscopy and an area containing tissue of interest marked on the wax block. Cylindrical cores (600 μM) were punch-biopsled from these representative areas and transferred into a recipient block. Tissue sampling used four cores from each tumor block to provide representative data on each parent block. A total of 108 core samples representing 26 patients were included per TMA block and two TMA blocks were constructed. Sections, 5 μM thick, were cut from the recipient TMA blocks and mounted on glass slides using a tape transfer system (Instrumedics, USA). H&E staining for verification of histology and sample integrity was performed on the first and every subsequent tenth section cut from each microarray block. TMA slides were then subject to immunohistochemical analyses.

Antibodies used included a mouse monoclonal antibody against NQO1 (provided by Drs. Siegel and Ross, University of Colorado Health Sciences Center, Denver, USA), a goat polyclonal antibody specific for P450R (Santa Cruz Biotechnology, USA), a mouse monoclonal antibody against Ki67 (BD Biosciences, UK) and a rabbit polyclonal antibody specific for glucose transporter-1 (GLUT-1; Dako, UK).

Immunolocalisation of NQO1, P450R, GLUT-1 and Ki67 was assessed by immunohistochemistry, as previously described and understood by those of ordinary skill in the art. Briefly, following antigen retrieval and blocking of non-specific immunoglobulin binding, TMAs were incubated with the appropriate primary antibody: incubated for about 60 minutes with the anti-NQO1 antibody diluted in 1:1 TBSTM (10 mM Tris-HCl, 150 mM NaCl, 0.2% Tween 20, 5% non-fat dry milk powder); incubated for about 90 minutes for P450R diluted 1:100 in PBS; incubated for about 90 minutes with the anti-Glut-1 antibody diluted 1:25 in PBS; or incubated overnight at 4° C. with the anti-Ki67 antibody diluted 1:100 in PBS. Controls were performed using normal IgG instead of primary antibody. Immunolocalisation was achieved using the appropriate biotinylated secondary antibody (diluted 1:200; Vector Labs., USA), followed by signal amplification using a Vectastain ABC kit (Vector Labs., USA) and visualization with 3,3'-diaminobenzidine (DAB) (Vector Labs., USA). Sections were then counterstained with Harris' hematoxylin, dehydrated, cleared and mounted in DPX mountant (Sigma, UK).

Positive immunostaining was scored semi-quantitatively by three independent observers. Both NQO1 and P450R were localised cytoplasmically within the tumor. A score for the epithelial compartment of each tumor core based on intensity and distribution of stain was assigned from 0 (no staining) to 4 (maximal staining intensity). An average scoring intensity was calculated for each core and each tumor of the TMA from the results of the independent observers. The results were compared for any relationships and correlations to clinicopathological parameters.

The level of Glut-1 positivity in each TMA core was analysed and assigned a score from 0 to 4 representative of the approximate percentage of tumor cells demonstrating membrane staining (0=no staining; 1=0-5% positive; 2=5-15% positive; 3=15-30% positive; 4=>30% positive). An average scoring intensity was calculated for each core and each tumor of the TMA from the results of the independent observers. The results were compared for any relationships and correlations to clinicopathological parameters.

The percentage Ki67 positive nuclei in the tumor cells was calculated using 40× magnification for each core and tumor, as reported by Santos et al. which is incorporated by reference herein. A total of 200 cells per core and 800 cells per tumor were counted and the percentage positivity calculated. The scoring was performed independently by two observers. The results were compared for any relationships and correlations to clinicopathological parameters.

The expression of NQO1 and P450R were compared with the following clinicopathological parameters: tumor stage, tumor grade, tumor hypoxia (Glut-1 expression) and proliferation. Statistical analysis was undertaken using the SPSS software package, version 11.0 (SPSS Inc., Chicago, Ill.). In the immunohistochemical study, because expression is not normally distributed, the average expression values for each category were reported as medians with interquartile ranges. Differences between independent variables were determined by the Mann-Whitney U test. Values of P less than 0.05 in two-tailed analyses were considered significant.

Relationship between NQO1 protein levels, tumor stage and grade. NQO1 was localised cytoplasmically in the epithelia of bladder tumors of all pathological grade and stage and expression of NQO1 varied between tumors (FIG. 1, Table 5). In many cases a heterogenous expression pattern of NQO1 was observed within the same tumor, with areas of high and low NQO1 expression within the same sample (data not shown). NQO1 was expressed in tumors of all pathological stage (pTa, pT1, ≥pT2) although expression levels of NQO1 varied between the various stages (Table 5). A significant difference in NQO1 expression was observed between superficial tumors (pTa+pT1) and muscle invasive tumors (≥pT2), with expression being significantly lower in muscle invasive tumors (P=0.02). The inverse relationship of NQO1 expression to tumor invasive potential is further reinforced by the significant difference in expression observed between non-invasive (pTa) and invasive (pT1+≥pT2) tumors (P=0.03). All pathological grades of TCC expressed NQO1 (Table 5). Expression of NQO1 was significantly higher in grade 2 tumors compared to either grade 1 or grade 3 (Table 5). No significant difference was observed between highly differentiated (grade 1) and poorly differentiated (grade 3) tumors (Table 5).

Relationship between P450R protein expression and tumor stage and grade. All tumors examined expressed detectable levels of P450R localised cytoplasmically. In contrast to NQO1, P450R expression was generally uniform within tumors. Representative immunostaining is depicted in FIG. 1. P450R was expressed in all stages of TCC (Table 5). Levels of P450R were significantly higher in muscle invasive tumors (≥pT2) compared to superficial (pTa+pT1) tumors (P<0.01).

In contrast to NQO1, expression of P450R shows a positive relationship to increasing tumor stage but is not associated with the invasive potential of the tumor, as is evident from the lack of significant difference observed between invasive (pT1+≥pT2) and non-invasive (pTa) tumors (Table 5). All pathological grades of TCC expressed P450R (Table 5). A positive correlation was observed between P450R levels and increasing tumor grade (Table 5).

Relationship between Glut-1 and tumor stage and grade. The expression of Glut-1 protein was heterogenous both within individual tumor specimens and between individual patient samples. Representative immunostaining and its relationship with tumor stage and grade are presented in FIG. 1 and Table 5 respectively. Glut-1 protein was expressed in all stages and grades examined although levels of Glut-1 were significantly higher in ≥pT2 tumors (relative to pTa tumors, P=0.05) and Grade 3 tumors (relative to both Grade 1 [P=0.03] and Grade 2 [P<0.01] tumors). In addition, statistically significant differences (P=0.02) exist between non-invasive (pTa) and invasive (pT1+≥pT2) tumors suggesting that invasive disease is associated with higher Glut-1 protein expression and consequently higher levels of hypoxia.

Relationship between Ki67, tumor stage, tumor grade and enzymology. Expression levels of Ki67 antigen were used as an indicator of tumor proliferative index (Table 5). As expected, a significant correlation was observed between increasing tumor grade (decreasing differentiation) and proliferation index (P<0.01). No relationship was observed between tumor proliferation and tumor invasive potential (pTa versus pT1+≥pT2). In contrast, tumor proliferation was significantly higher in muscle invasive tumors (≥pT2) relative to superficial tumors (pTa+pT1 [P<0.01]) probably as a result of the relationship between muscle invasion and higher tumor grade. Interestingly, a significant relationship was observed between tumor proliferative index and both Glut-1 expression (P=0.01) and P450R expression (P<0.01), but not NQO1 expression.

The results of this study demonstrate that the protein expression of key enzymes involved in the bioreductive activation of quinone based compounds and the presence of hypoxia as determined by Glut-1 protein levels changes with stage and grade of bladder TCC. The most striking observation is the fact that NQO1 protein expression decreases significantly with increasing tumor stage (Table 5). With regards to tumor grade, there is also evidence that G3 tumors have lower levels of NQO1 than G2 (but not G1) tumors. These findings are in agreement with previously published studies where an inverse relationship between NQO1 mRNA expression and increasing tumor stage was reported. Similarly for Glut-1, increased protein expression with tumor grade (P=0.03 and <0.01 when G1 and G2 was compared with G3 tumors respectively) and tumor stage (P=0.05 when pTa tumors are compared to ≥pT2 tumors) is consistent with previous reports. In contrast to previously published reports demonstrating higher levels of P450R mRNA in superficial compared to muscle-invasive TCC, P450R protein levels were significantly higher in muscle-invasive (≥pT2 compared to pTa+pT1) disease in this study (P<0.01). In addition, P450R protein expression shows a positive correlation with increasing tumor grade (decreasing differentiation) (Table 5). Interestingly, P450R expression also demonstrated a strong positive correlation to proliferation index (P<0.01), probably as a consequence of a strong relationship between P450R, Ki67 and increasing tumor grade (decreasing differentiation). Nevertheless, this should be borne in mind when evaluating bioreductive therapies involving P450R since high proliferative index has been shown to relate to poor prognosis in bladder cancer. In summary, analysis of protein expression by immunohistochemistry suggests that hypoxia, as demonstrated by Glut-1 expression, relates to increasing tumor stage, grade and tumor invasion. With reference to tumor enzymology, this study suggests NQO1 levels significantly decrease as a function of increasing tumor stage (and invasive potential) whereas P450R levels increase with tumor grade and invasive potential.

These findings have significant implications for potential therapeutic strategies using quinone based bioreductive drugs in the treatment of bladder TCC. There is extensive evidence in preclinical models indicating that the response of cells to MMC, Apaziquone and RH1 is dependent not only on NQO1 levels but also on the level of tumor hypoxia. With regards to MMC, the role of NQO1 in determining cellular response under aerobic conditions is controversial but under hypoxic conditions, significant potentiation of activity is seen only in cells that have low or no NQO1 activity. In the case of Apaziquone and RH1, similar results have been obtained under hypoxic conditions with marked potentiation of activity observed only in cells with low NQO1. Under aerobic conditions however, there is a good correlation between NQO1 activity and chemosensitivity suggesting that in the presence of oxygen, NQO1 plays a prominent role in activating Apaziquone and RH1. The mechanistic basis to explain these observations is not clear but under hypoxic conditions, one electron reductases such as P450R assume a more influential role in the bioreductive activation process (25). Based on these findings, compounds such as Apaziquone and RH1 would target the aerobic fraction of NQO1 rich tumors (and so would MMC but to a lesser extent) or the hypoxic fraction of NQO1 deficient tumors assuming that one electron reductases such as P450R are present. In the case of NQO1 rich tumors therefore the use of compounds such as Apaziquone and RH1 as single agents targeting the aerobic fraction would be appropriate. For NQO1 deficient tumors with a significant hypoxic fraction, these agents should be used in combination with radiotherapy or other chemotherapeutic agents that target the aerobic fraction. The results of this study suggest that this latter strategy may be effective in the case of more advanced TCC of the bladder (i.e. ≥pT2) or more aggressive disease (i.e. Grade 3 tumors) as these typically have low NQO1 protein expression (and possibly greater P450R expression) and contain significant areas of hypoxia. In this specific context, it is of interest to note that encouraging results have been obtained in muscle invasive bladder cancer using chemoradiotherapy (Mitomycin C plus 5 Fluorouracil in combination with radical radiotherapy) although analysis of NQO1 and hypoxia markers was not incorporated into the design of this study. In the broader context, the demonstration in this and other studies that both superficial and muscle invasive bladder TCC have significant regions of hypoxia suggests that these tumors are attractive candidates for evaluating other bioreductive drugs or hypoxia mediated therapies.

In conclusion, the results of this study have demonstrated that the protein expression of key enzymes involved in the bioreductive activation of quinone based compounds and the presence of hypoxia changes as a function of tumor stage and grade in TCC of the bladder. These results suggest that these tumors (i.e. ≥pT2 and G3 tumors) would be good candidates for chemo-radiotherapy regimens using quinones (e.g. MMC, Apaziquone and RH1) to target the hypoxic fraction in combination with radiation or other chemotherapeutics to target the aerobic fraction of cells. Based on these rationales, and referring back to FIG. 1, case A ($pT_2$ G3) demonstrates low NQO1, high P450R and High Glut-1 levels and therefore would be a good candidate for chemoradiotherapy using quinones. Case B (pTa G1) has high NQO1, low P450R and moderate Glut-1 and as such should respond well to quinone based chemotherapy. Case C ($pT_1$ G2) which has moderate NQO1, moderate P450R and moderate Glut-1 would also be predicted to respond well to quinone based chemotherapy. Profiling of individual patients tumors for these markers remains important, particularly in view of the marked inter-patient heterogeneity (particularly with NQO1) that exists.

As used herein, when using enzyme levels to determine an appropriate treatment for a patient, "high" versus "low" levels of the enzyme can be ascertained by comparing levels of the enzyme of interest from the relevant tumor to other tumors from the same patient, to tumors from another patient and/or to standard tumor cell lines or other available reference points known to those of ordinary skill in the art. Thus, "high" and "low" levels can be determined by a treating physician or other laboratory, research or treatment personnel involved in measuring and/or quantitating a particular patient's tumor enzyme levels.

Example 4

Figures 2, 3:
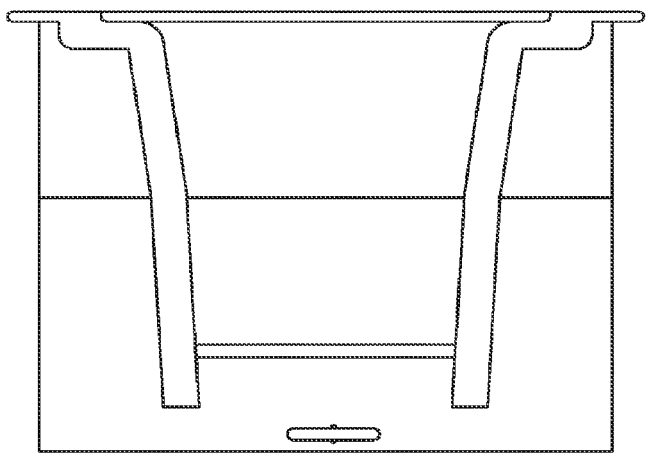
FIG. 2 shows the apparatus used to study drug penetration through multicell layers.
FIG. 3 shows a schematic representation of drug solution preparations.

As shown in FIG. 2, the apparatus used in the described experiment comprised a transwell insert (Costar) inserted into one well of a 24 well culture plate. The insert had a collagen coated membrane at its base and thus formed both a barrier between the top and bottom chamber as well as a surface upon which cells could attach and grow. The cell line used in this study was DLD-1 human colon adenocarcinoma cells which was selected because of its ability to form tight junctions between cells thereby forming a continuous 'barrier' across which the drug must cross. To assess drug penetration, drugs were added to the top chamber and the concentration of drug in the bottom chamber was determined over a range of time intervals.

DLD-1 cells were routinely maintained in RPMI 1640 medium supplemented with 10% fetal calf serum, sodium pyruvate (1 mM), L-glutamine (2 mM), penicillin/streptomycin (50 IU/ml, 50 µg/ml) and buffered with HEPES (25 mM). DLD-1 cells ($2.5 \times 10^5$ in 200 µl of medium) were added to the top chamber and allowed to settle and attach to the membrane for approximately 3 hours at 37° C. in a $CO_2$ enriched (5%) atmosphere. Once cells attached, the transwell was inserted into one well of a 24 well plate and 600 µl media was added to the bottom chamber. The apparatus was then incubated at 37° C. for 4 days with daily media changes to both the upper and lower chamber. Based upon previous studies, the thickness of the multicell layer after 4 days of culture is approximately 50 µm. For each assay, 3 transwells were removed for histological examination and accurate determination of thickness and integrity (see below for details).

The following solutions were prepared as described below and summarized in FIG. 3.

Solution 1: Apaziquone (347 µM) in 0.1% DMSO. Solid Apaziquone was dissolved in 100% DMSO to make a stock solution of 347 mM. 10 µl of the stock solution were added into 10 ml of complete RPMI medium (phenol red free). In order to prevent a possible precipitation of Apaziquone, the addition of Apaziquone stock solution into the medium was with a continuous shaking. The final concentration of Apaziquone was 347 µM which is equivalent to 4 mg/40 ml.

Solution 2: Apaziquone (347 µM) in 10% propylene glycol. Two hundred milligrams of sodium bicarbonate ($NaHCO_3$) were dissolved in 4 ml of EDTA solution (0.5 mg/mL, which was prepared fresh from 0.5 M stock solution, Sigma). The solution was then mixed with 6 ml propylene glycol solution (2 ml propylene glycol+4 ml $H_2O$) making a final volume of 10 ml containing 20% propylene glycol. This solution was added into 20 ml universal tube containing Apaziquone (2 mg), sodium bicarbonate (5 mg) and mannitol (12.5 mg). The solution was incubated at 37° C. with continuous shaking until the Apaziquone was completely dissolved (about 5-6 hours). Then, the solution was diluted 1:1 with water to yield 10% propylene glycol, solution.

Solution 3: Apaziquone (347 µM) in 20% propylene glycol. Two hundred milligrams of sodium bicarbonate (NaHCO$_3$) were dissolved in 4 ml of EDTA solution (0.5 mg/mL, which was prepared fresh from 0.5 M stock solution, Sigma). The solution was then mixed with 6 ml propylene glycol solution (4 ml propylene glycol+2 ml H$_2$O) making a final volume of 10 ml containing 40% propylene glycol. This solution was added into 20 ml universal tube containing Apaziquone (2 mg), sodium bicarbonate (5 mg) and mannitol (12.5 mg). The solution was incubated at 37° C. with continuous shaking until the Apaziquone was completely dissolved (about 3-4 hours). Then, the solution was diluted 1:1 with water to yield 20% propylene glycol, solution.

Solution 4: Apaziquone (347 µM) in 30% propylene glycol. Two hundred milligrams of sodium bicarbonate (NaHCO$_3$) were dissolved in 4 ml of EDTA solution (0.5 mg/mL, which was prepared fresh from 0.5 M stock solution, Sigma). The solution was then mixed with 6 ml propylene glycol (6 ml propylene glycol+0 ml H$_2$O) making a final volume of 10 ml containing 60% propylene glycol. This solution was added into 20 ml universal tube containing Apaziquone (2 mg), sodium bicarbonate (5 mg) and mannitol (12.5 mg). The solution was incubated at 37° C. with continuous shaking until the Apaziquone was completely dissolved (about 2 hours). Then, the solution was diluted 1:1 with water to yield 30% propylene glycol, solution.

Throughout all procedures, the media used was as described above except for the fact that phenol red free media was used (phenol red elutes very close to Apaziquone on the chromatograms). Apaziquone was added to the top chamber at t=0 in a volume of 100 µl and the bottom chamber contained 600 µl of media (constantly stirred). Following a 10 minute incubation at 37° C., the transwell was removed and placed into a new well of the 24 well plate containing 600 µl of fresh media. The drug solution in the top chamber was removed and replaced with 100 µl of fresh drug solution (i.e., the concentration in the top chamber was maintained at a constant concentration). This whole procedure was repeated at 10 minute intervals over a total time period of 1 hour.

Apaziquone was immediately extracted using Isolute C18 SPE cartridges. Cartridges were primed with 1 ml methanol followed by washing in 1 ml deionised water prior to sample addition (500 µl). Following a further washing in 1 ml deionised water, Apaziquone was eluted in 300 µl methanol. Samples were dried under vacuum (at room temperature in a rotary evaporator) and either stored at −20° C. until required for analysis or reconstituted in mobile phase (see below) for immediate analysis.

Chromatographic analysis of Apaziquone was carried out as described by Phillips et al. (British Journal of Cancer. 65(3):359-64, 1992) which is incorporated by reference herein. Briefly, a Hichrom RPB column (25 cm×4.6 mm id, Hichrom Ltd, UK) was used for the separation. A Waters 996 Photodiode Array Detector ($\lambda_1$=280 nm,) with Masslynx 3.4 software (Micromass Ltd) was used for spectral analysis of the peaks of interest. The mobile phase consisted of 1M phosphate buffer (1%), methanol (42%) and HPLC grade water (57%). The flow rate was set at 1.2 ml min$^{-1}$ using a Waters Alliance 2690 (Milford, Mass., USA) quaternary pump chromatography system, which also incorporates the autosampler. The detection limit was 10 ng/ml (34.7 nM).

For each experiment, 3 transwell inserts were collected; 1 control and 2 at the end of the experiment. Each transwell was fixed in 10% formalin for one hour prior to transfer to 70% ethanol and storage overnight. Using a clean scalpel, the membranes were carefully detached from the plastic insert and processed for embedding in paraffin wax using standard procedures known to those of ordinary skill in the art. Specimens were sectioned (5 µm) using a Leitz rotary microtone, mounted onto protein coated glass slides and stained using haemotoxylin and eosin also using standard procedures known to those of ordinary skill in the art. The thickness of the multicell layer was measured using an eyepiece graticule that had been calibrated using a stage micrometer. Five measurements were obtained for each section and 3 sections per sample were measured.

Figure 4:
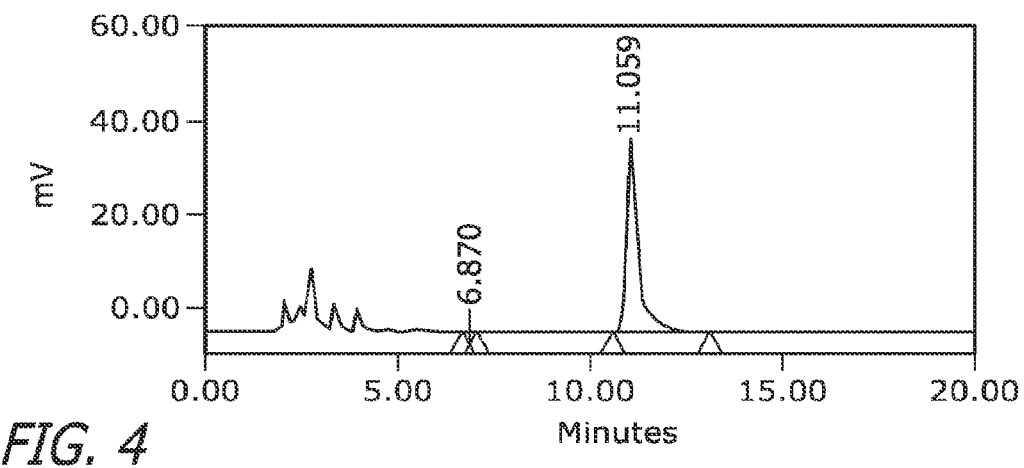
FIG. 4 shows a chromatogram of blank sample spiked with WV14 as an internal standard.
Figure 5A:
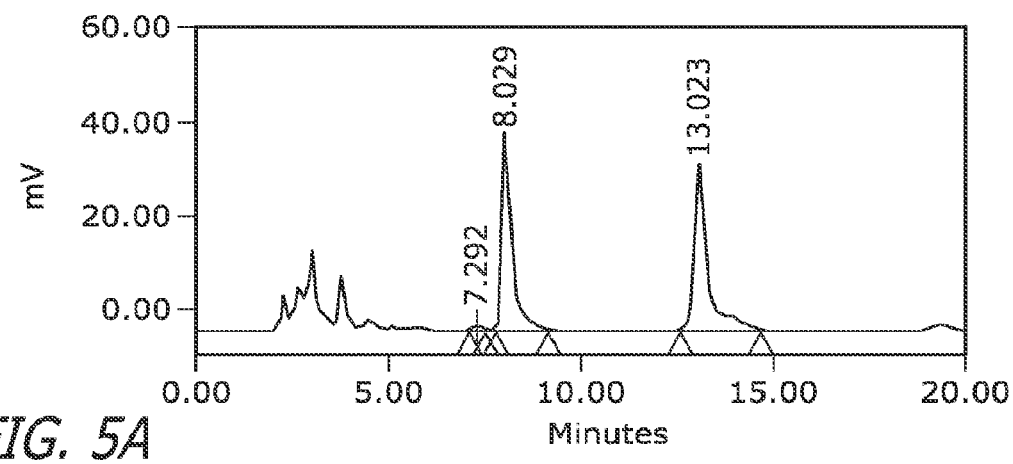
FIG. 5 shows chromatograms of Apaziquone standard in RPMI 1640 culture.
Figure 5B:
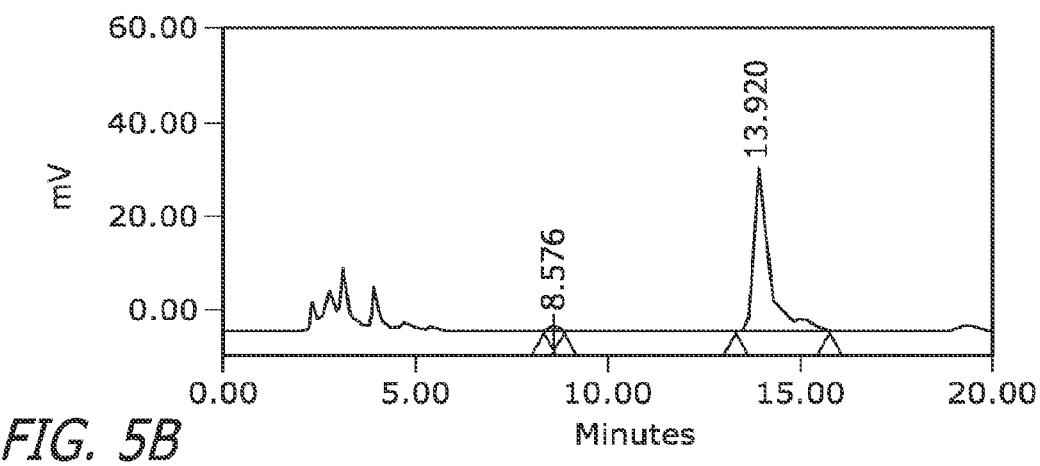
Figure 6A:
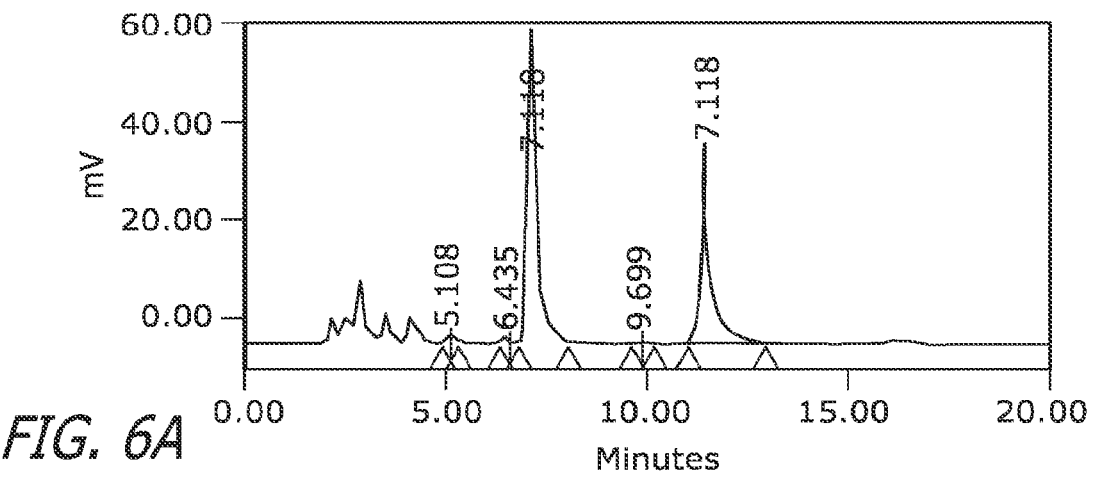
FIG. 6 shows chromatograms of Apaziquone standards in 0.1% DMSO (6A); 30% propylene glycol (propylene glycol; 6B); 20% propylene glycol (6C); and 10% propylene glycol (6D).
Figure 6B:
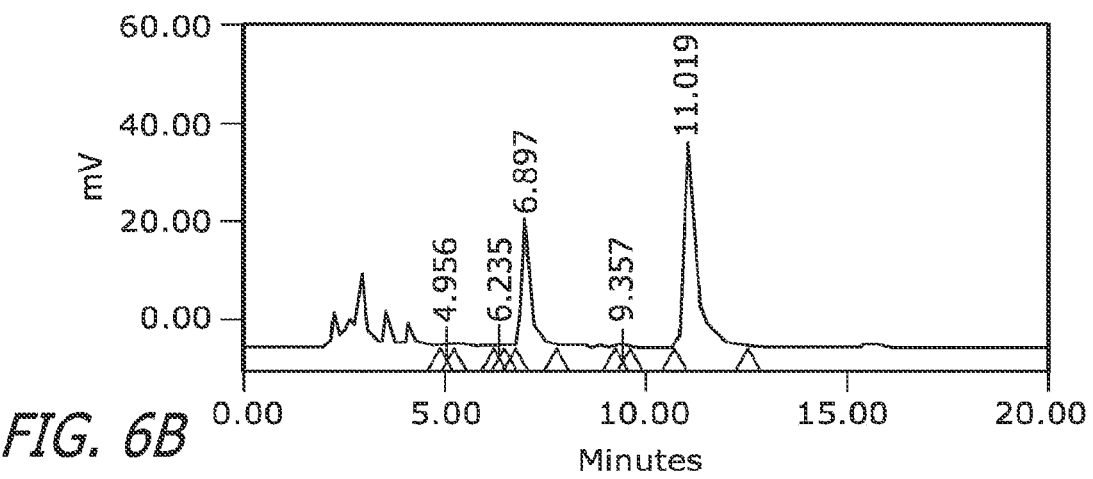
Figure 6C:
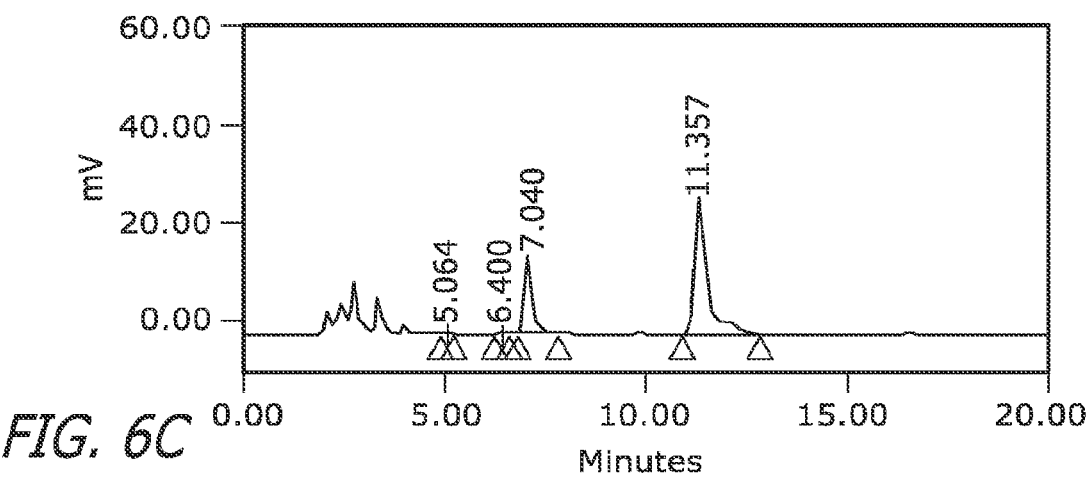
Figure 6D:
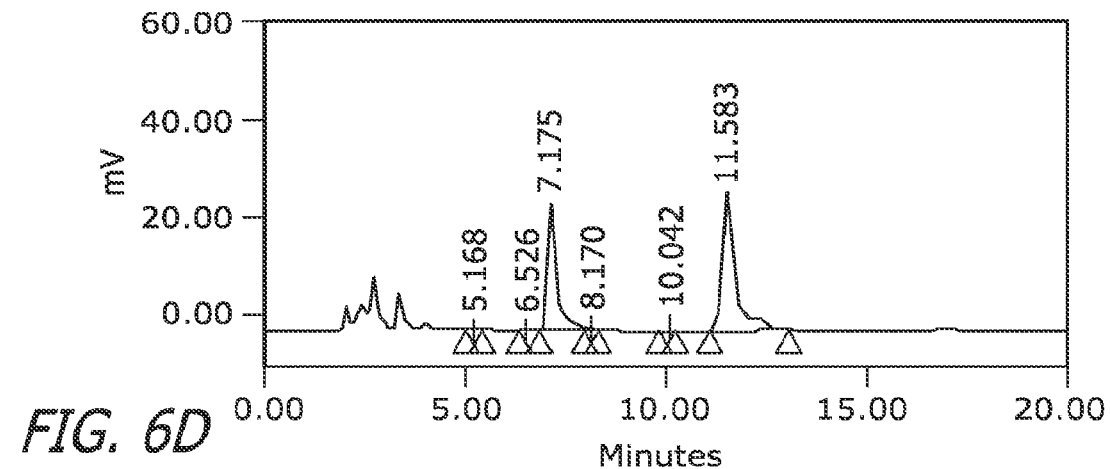

FIG. 4 shows a chromatogram of a blank sample spiked with WV14 internal standard (retention time=11.059 minutes). The peak at 6.870 minutes is a contaminating peak. FIG. 5 shows Apaziquone standards (1 µg/ml (FIG. 5A) and 20 ng/ml (FIG. 5B)) in RPMI 1640 culture medium. As shown in FIG. 5A, the Apaziquone and WV14 peaks elute at 8.029 minutes and 13.023 minutes respectively (the peak at 7.292 min is the contaminating peak described above). It should be noted that retention times can move due to temperature fluctuations in a laboratory but that relative retention times should remain constant. FIG. 5B indicates the limit of detection. FIG. 6 shows chromatograms of Apaziquone standards in 0.1% DMSO (FIG. 6A); 30% propylene glycol (FIG. 6B); 20% propylene glycol (FIG. 6C); and 10% propylene glycol (FIG. 6D).

Figure 7:
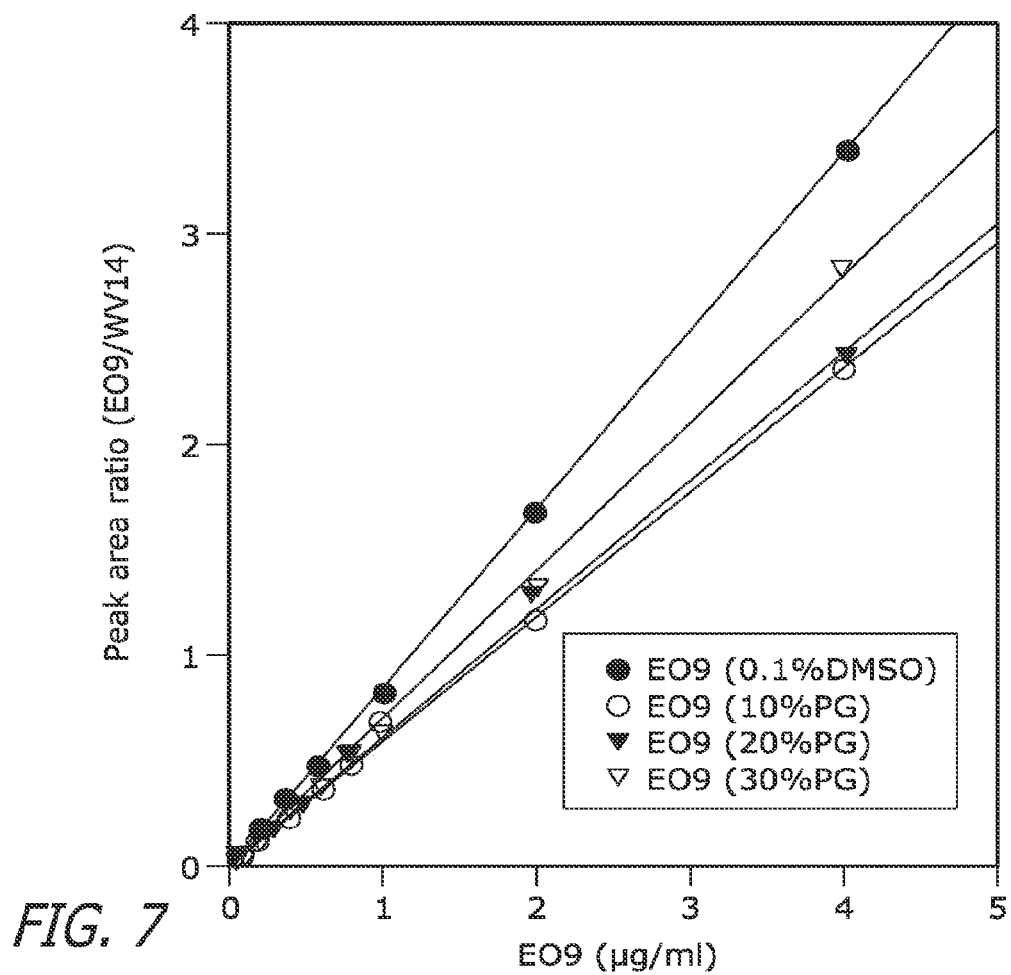
FIG. 7 shows calibration curves for Apaziquone in 0.1% DMSO and various propylene glycol (30%; 20%; 10%) concentrations.

Calibration curves were constructed for each Apaziquone preparation and the results are presented in FIG. 7. Calibration curves were reproducible and subtle differences in the slope of each calibration curve were observed as illustrated in FIG. 7. The reasons for the differences are unclear but may reflect slight differences in extraction efficiency between the different preparations. The extraction efficiencies for Apaziquone in 0.1% DMSO, 10% propylene glycol, 20% propylene glycol and 30% propylene glycol were 92.3%, 81.7%, 79.9% & 81.1% respectively. Because of this variation, calibration curves were generated for each experiment conducted. No obvious breakdown products were visible on any of the chromatograms.

Figure 8:
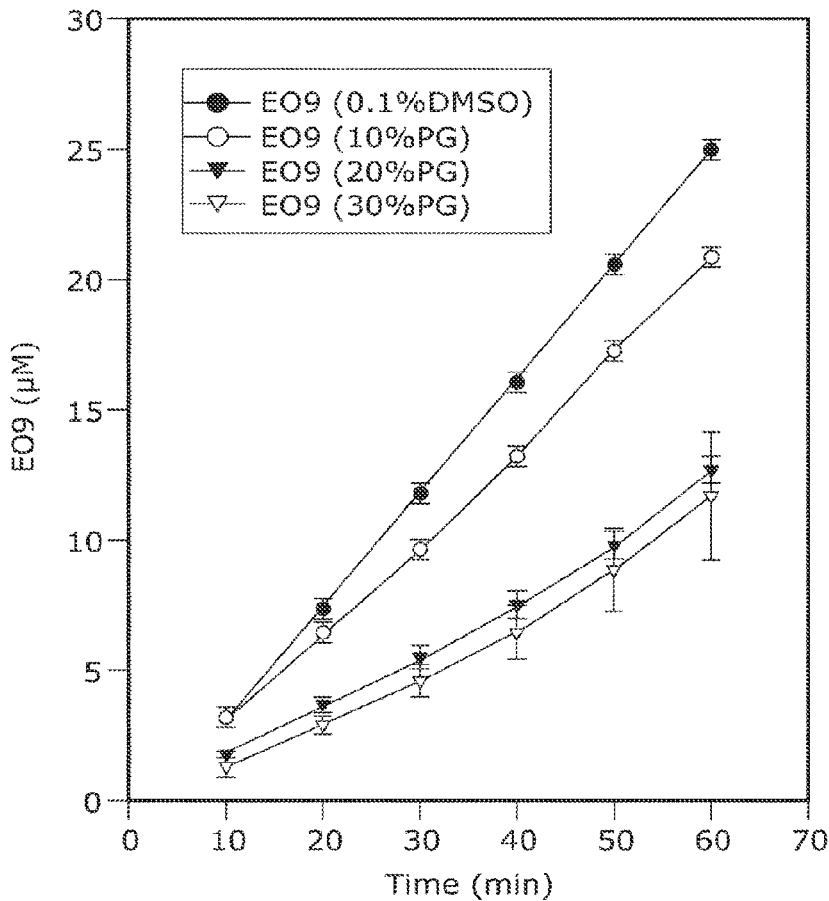
FIG. 8 shows the penetration of Apaziquone in various propylene glycol concentrations through DLD-1 multicell layers.

As can be seen in FIG. 8, as the concentration of propylene glycol increases, the multicell layer penetration rate of Apaziquone decreases. With regard to Apaziquone in 0.1% DMSO, the kinetics is linear which is as expected when the concentration in the top chamber is maintained at a more or less constant value. At the two highest concentrations of propylene glycol tested, it is worth noting that the kinetics are not quite linear—there is a progressive increase in rate as time increases. This effect probably reflects the changes in the thickness of the multicell layer induced by propylene glycol (see FIG. 9). No obvious metabolites or breakdown products were observed at any of the evaluated time points.

Figure 9:
FIG. 9 shows representative cross sections through stained DLD-1 multicell layers.
Figure 9:
Figure 9:

FIG. 9 shows the results of histological analyses undertaken to examine the penetration of Apaziquone through DLD-1 multicell layers. The thickness of non-drug treated sections was 56.01±3.63 µm. After one hour of treatment with Apaziquone in 0.1% DMSO, the thickness of the multicell layer was not significantly different from non-drug treated specimens (58.80±2.50 µm). Following treatment with Apaziquone in 30% propylene glycol however, the thickness of the multicell layer decreased significantly to 29.01±1.78 µm. There were also marked morphological changes in appearance within the layer, the most obvious of which was the appearance of 'breaks' or 'channels' in the layer itself. An observation made throughout experiments using Apaziquone in propylene glycol was that the upper chamber contained more fluid than expected. For example, after a 10 min incubation with Apaziquone in propylene glycol at 30%, 20% and 10%, the volume recovered from the top chamber was 106±3, 107±3 and 105±2 μl respectively (after a one hour exposure to Apaziquone in 0.1% DMSO, the volume recovered was 98±2 μl). It should be stressed that these volumes are only approximations (being based on what could be recovered using a Gilson pipette) but they do indicate that the volume of media in the upper chamber changes when Apaziquone dissolved in propylene glycol formulations (especially at 30% propylene glycol) is used. It is also noteworthy that the histological pictures show that cells are in close contact with the basement membrane in controls and Apaziquone (0.1% DMSO) treated specimens but for multicell layers treated with Apaziquone in 30% propylene glycol, there is a small but distinct gap between the multicell layer and the membrane itself.

described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be

TABLE 5

Protein expression of NQO1, P450R, GLUT-1 and Ki67 in human TCC of the bladder.

| Grade | Number of Samples | Median NQO1 expression (± interquartiles) | Median P450R expression (± interquartiles) | Median GLUT-1 expression (± interquartiles) | % proliferation (Ki67 positive) (± S.E.) |
|---|---|---|---|---|---|
| pTa | 19 | 2.50 (1.14-3.20) | 3.20 (2.58-3.83) | 2.00 (1.30-3.80) | 16.75 ± 2.8 |
| $pT_1$ | 19 | 1.88 (0.33-3.00) | 2.96 (2.33-3.67) | 3.38 (2.75-3.88) | 13.88 ± 2.2 |
| $pT_2$ | 14 | 0.17 (0.00-1.67) | 3.89 (3.75-3.92) | 3.88 (2.67-4.00) | 24.59 ± 4.43 |
| G1 | 11 | 1.00 (0.00-1.10) | 2.79 (2.17-2.92) | 2.38 (2.00-3.25) | 9.72 ± 2.64 |
| G2 | 26 | 2.72 (1.83-3.20) | 3.35 (2.75-3.83) | 2.83 (1.75-3.75) | 14.59 ± 1.72 |
| G3 | 15 | 0.33 (0.00-1.85) | 3.83 (3.31-3.92) | 4.00 (3.63-4.00) | 30.47 ± 3.71 |
| Non-invasive[a] | 19 | 2.50 (1.14-3.20) | 3.20 (2.58-3.83) | 2.00 (1.31-3.67) | 17.51 ± 2.83 |
| Invasive[b] | 33 | 1.67 (0.0-2.52) | 3.67 (2.92-3.89) | 3.50 (2.71-4.00) | 19.41 ± 2.86 |
| Superficial[c] | 38 | 2.00 (1.08-3.17) | 3.10 (2.33-3.78) | 2.83 (1.83-3.83) | 15.69 ± 1.79 |
| Muscled Invasive[d] | 14 | 0.17 (0.00-1.67) | 3.89 (3.75-3.92) | 3.88 (2.67-4.00) | 24.59 ± 4.43 |

The suffixes a b, c and d denote pTa; ($pT_1 + pT_2$); (pTa + $pT_1$) and $pT_2$ tumour stages respectively.
Data for NQO1, P450R and GLUT-1 are presented as the median score (± interquartile range) of two observers.
Data for proliferation index are presented as mean score ± S.E of two observers.
Specimens were rated between 0 and 4 for NQO1, P450R and GLUT-1 and proliferation index was calculated as % Ki67 positivity.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A pharmaceutical preparation comprising Apaziquone, propylene glycol, sodium bicarbonate, mannitol, EDTA and water wherein the concentration of propylene glycol is about 30% (v/v), about 20% (v/v), or about 10% (v/v).

2. The pharmaceutical preparation according to claim 1, wherein said Apaziquone is present in a concentration of between about 300 µM to about 400 µM.

3. The pharmaceutical preparation according to claim 1, wherein said Apaziquone is present in a concentration of about 347 µM.

4. The pharmaceutical preparation according to claim 1, wherein said mannitol is present in a concentration of between about 0.5 mg/mL to about 3.0 mg/mL.

5. The pharmaceutical preparation according to claim 4, wherein said mannitol is present in a concentration of about 1.25 mg/mL.

6. A pharmaceutical preparation comprising Apaziquone, propylene glycol, $NaHCO_3$, mannitol, EDTA and water wherein said propylene glycol is present in a range of about 6% (v/v) to about 14% (v/v), about 16% (v/v) to about 24% (v/v), or about 26% (v/v) to about 34% (v/v).

7. The pharmaceutical preparation according to claim 6, wherein said propylene glycol is present in a concentration of about 10% (v/v), about 20% (v/v), or about 30% (v/v).

8. The pharmaceutical preparation according to claim 6, wherein said preparation comprises about 347 µM Apaziquone and about 10% (v/v) propylene glycol.

9. The pharmaceutical preparation according to claim 6, wherein said preparation comprises about 347 µM Apaziquone and about 20% (v/v) propylene glycol.

10. The pharmaceutical preparation according to claim 6, wherein said preparation comprises about 347 µM Apaziquone and about 30% (v/v) propylene glycol.

11. The pharmaceutical preparation according to claim 6, wherein said preparation comprises about 0.5 mg/mL to about 3.0 mg/mL mannitol.

12. The pharmaceutical preparation according to claim 11, wherein said preparation comprises about 1.25 mg/mL mannitol.

* * * * *